US010653827B2

(12) United States Patent
Takeuchi et al.

(10) Patent No.: US 10,653,827 B2
(45) Date of Patent: May 19, 2020

(54) BLOOD PURIFICATION APPARATUS

(71) Applicant: Nikkiso Company Limited, Tokyo (JP)

(72) Inventors: Satoshi Takeuchi, Shizuoka (JP); Kazuya Tsuji, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 43 days.

(21) Appl. No.: 15/952,419

(22) Filed: Apr. 13, 2018

(65) Prior Publication Data

US 2018/0228961 A1 Aug. 16, 2018

Related U.S. Application Data

(63) Continuation of application No. PCT/JP2016/082074, filed on Oct. 28, 2016.

(30) Foreign Application Priority Data

Oct. 29, 2015 (JP) ................................ 2015-212822

(51) Int. Cl.
*A61M 1/36* (2006.01)
*A61M 1/34* (2006.01)
(Continued)

(52) U.S. Cl.
CPC .......... *A61M 1/3656* (2014.02); *A61M 1/267* (2014.02); *A61M 1/342* (2013.01);
(Continued)

(58) Field of Classification Search
None
See application file for complete search history.

(56) References Cited

U.S. PATENT DOCUMENTS 4,493,693 A     1/1985   Bilstad et al.
4,617,115 A  *  10/1986  Vantard .................... A61M 1/16
                                                         210/321.77
(Continued)

FOREIGN PATENT DOCUMENTS

DE        10218846 C1     4/2002
JP        2011-161060 A   8/2011
(Continued)

OTHER PUBLICATIONS

International Search Report from the Japanese Patent Office for Application No. PCT/JP2016/082074 dated Dec. 13, 2016.
(Continued)

*Primary Examiner* — Richard C Gurtowski
(74) *Attorney, Agent, or Firm* — Young Basile Hanlon & MacFarlane, P.C.

(57) ABSTRACT

The present teachings relate to a blood purification apparatus in which the connection of a substitution line to a collecting port can be checked accurately and instantly and even during blood purification treatment. A blood purification apparatus includes a blood circuit, a dialyzer, a dialysate introduction line, a dialysate drain line, a substitution line one end of which is connected to a collecting port provided at a predetermined position of the dialysate introduction line and an other end of which is connected to the blood circuit, a substitution pump configured to form a pressure-increasing portion that includes the collecting port, and a pressure-measuring device capable of measuring a pressure in the pressure-increasing portion. The blood purification apparatus performs a testing process by increasing a liquid pressure in the pressure-increasing portion by utilizing a liquid-feeding pressure applied from a liquid-feeding device and measuring the pressure with the pressure-measuring device.

19 Claims, 20 Drawing Sheets

(51) Int. Cl.
*A61M 1/26* (2006.01)
*F16K 37/00* (2006.01)
*G01M 3/28* (2006.01)
*A61M 1/16* (2006.01)

(52) U.S. Cl.
CPC ....... A61M 1/3638 (2014.02); F16K 37/0041 (2013.01); G01M 3/2853 (2013.01); *A61M 1/1656* (2013.01); *A61M 1/3639* (2013.01); *A61M 2205/15* (2013.01); *A61M 2205/3317* (2013.01); *A61M 2205/3337* (2013.01); *A61M 2205/702* (2013.01)

(56) References Cited

U.S. PATENT DOCUMENTS

| 4,828,543 | A | * | 5/1989 | Weiss | A61M 1/16 210/637 |
| 6,960,179 | B2 | * | 11/2005 | Gura | A61M 1/16 210/321.8 |
| 7,004,924 | B1 | * | 2/2006 | Brugger | A61M 1/3626 600/16 |
| 2002/0104800 | A1 | | 8/2002 | Collins et al. | |
| 2011/0098625 | A1 | * | 4/2011 | Masala | A61M 1/342 604/6.09 |
| 2013/0028788 | A1 | | 1/2013 | Gronau et al. | |
| 2013/0030347 | A1 | * | 1/2013 | Sugioka | A61M 1/342 604/6.09 |
| 2014/0216250 | A1 | * | 8/2014 | Meyer | A61M 1/1658 95/22 |

FOREIGN PATENT DOCUMENTS

| JP | 2012-192101 A | 10/2012 |
| JP | 2012-200340 A | 10/2012 |

OTHER PUBLICATIONS

Extended European Search Report dated Jun. 13, 2019, Application No. 16859958.7.

* cited by examiner

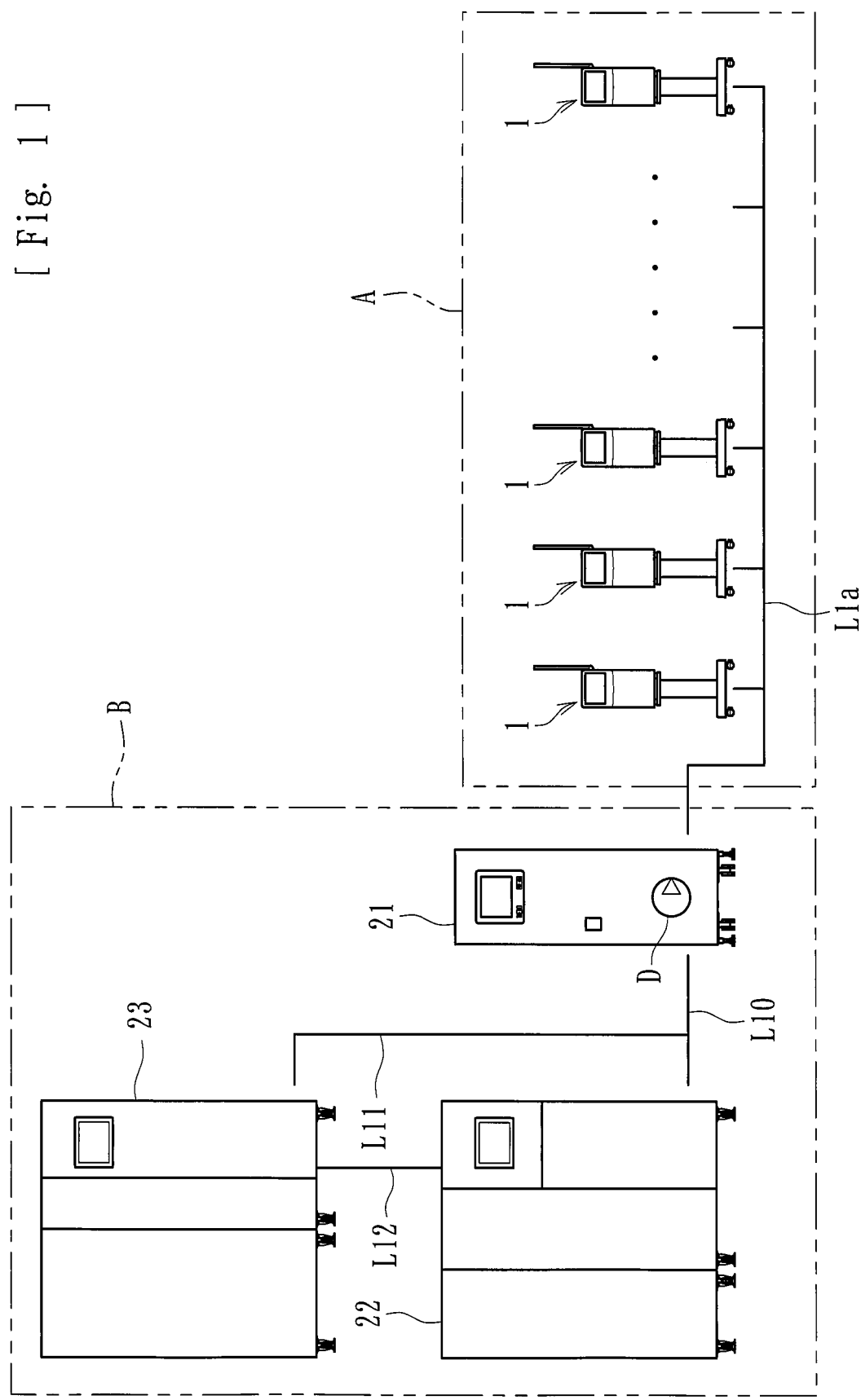

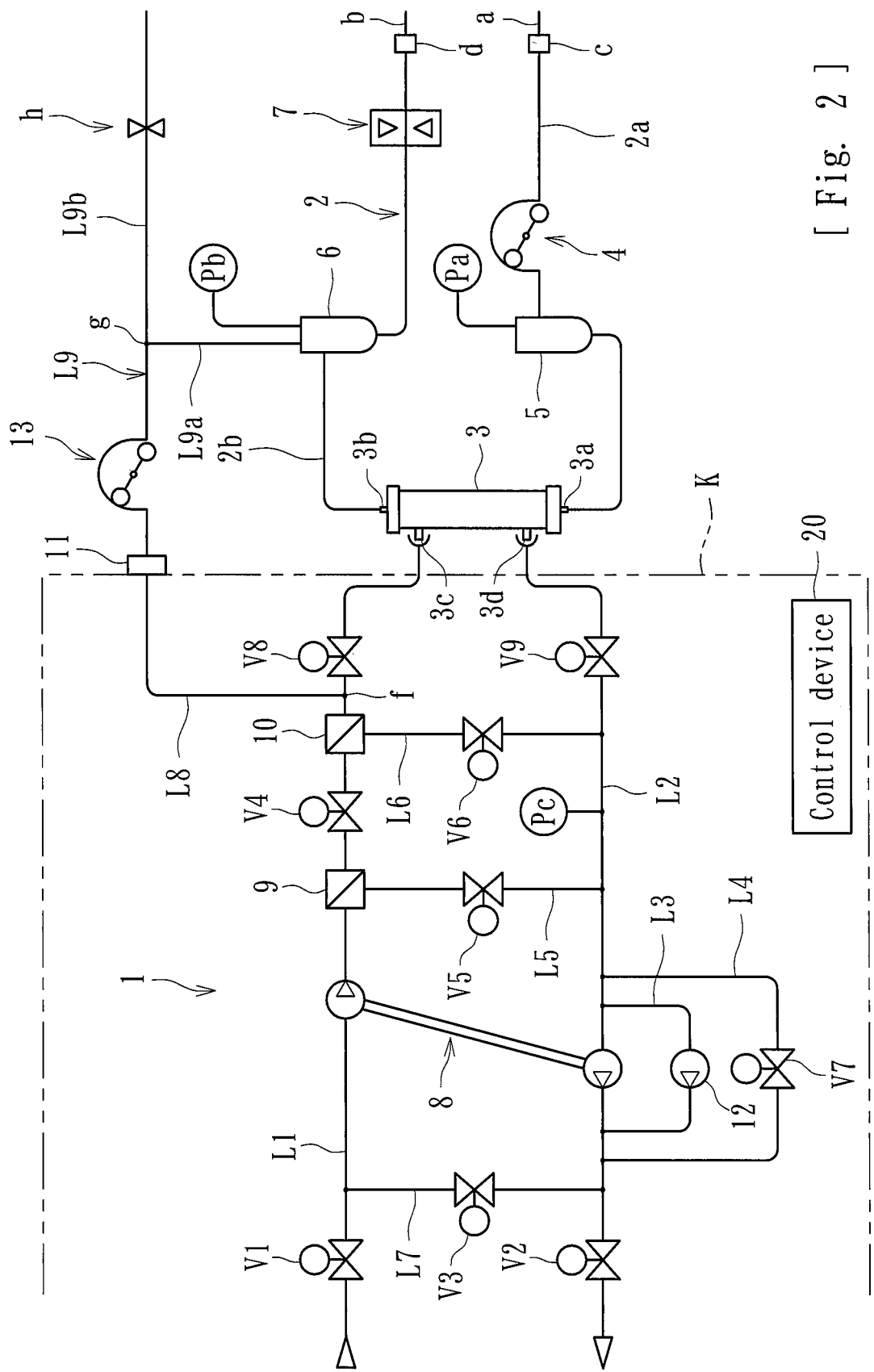
[Fig. 2]

[Fig. 3]
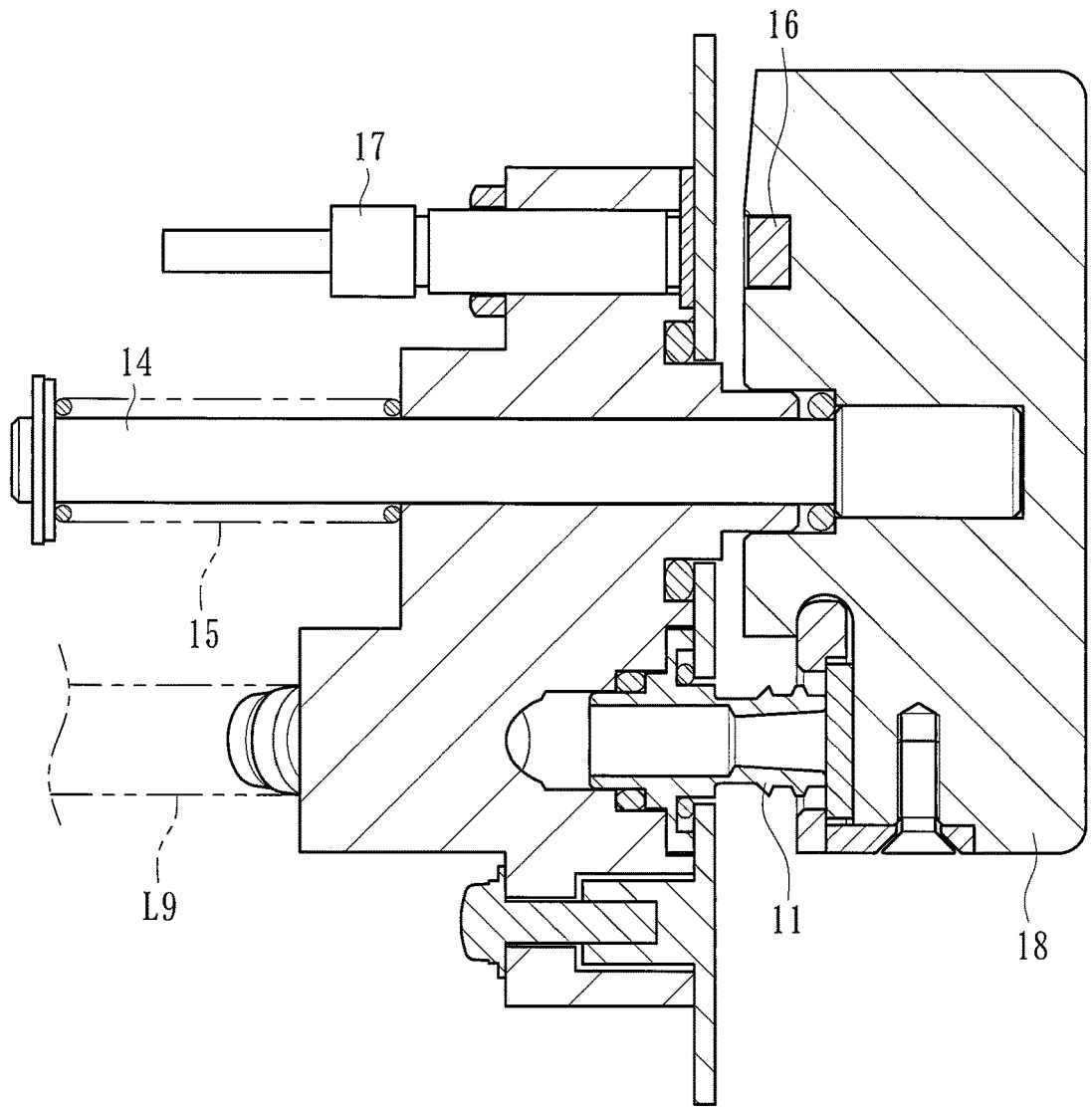
[Fig. 4]
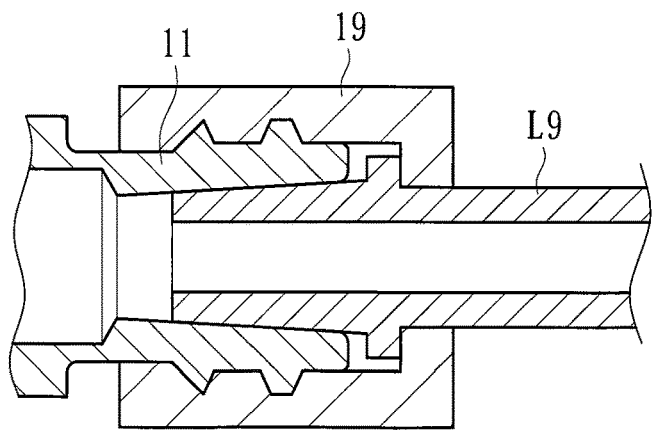

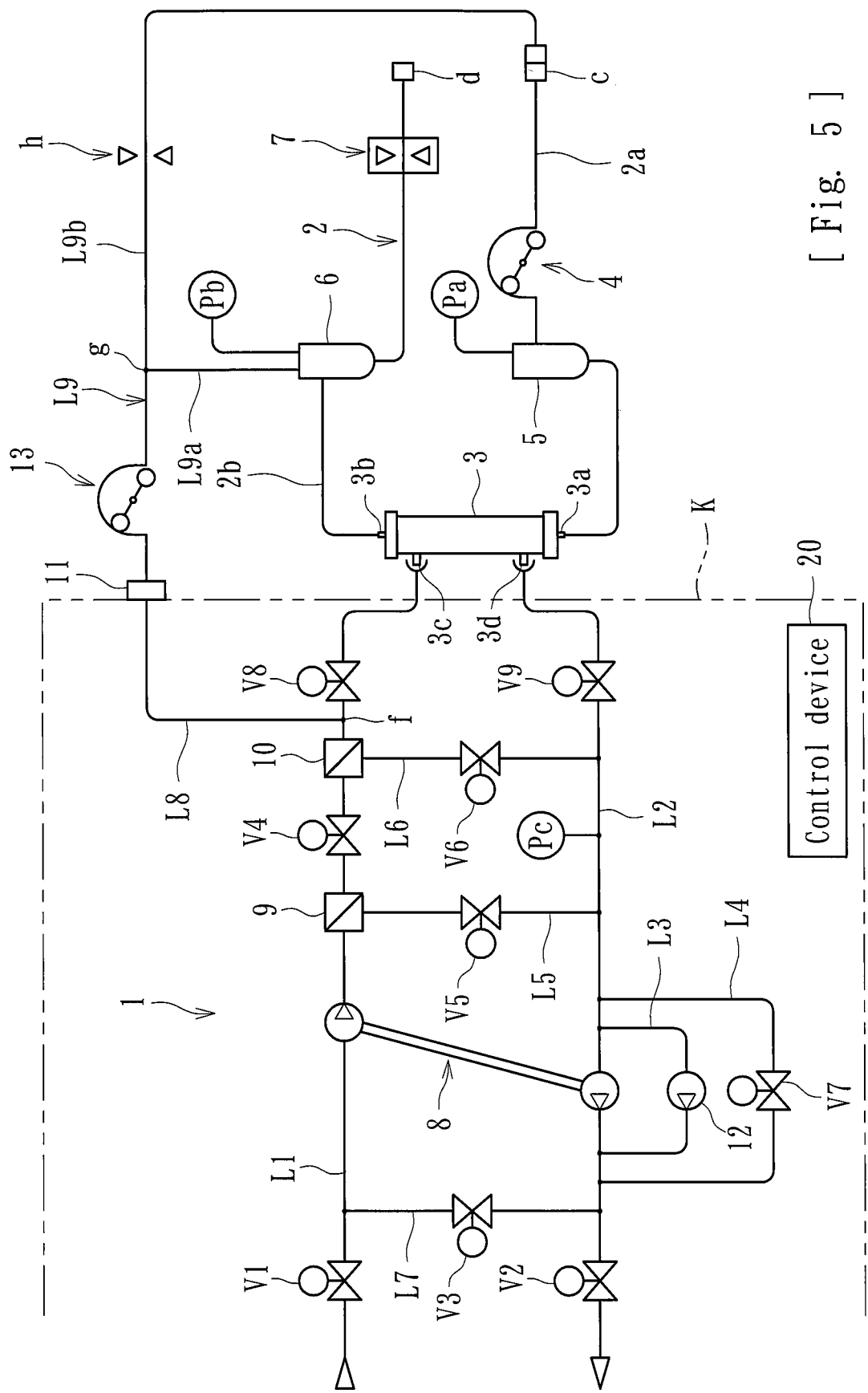
[Fig. 5]

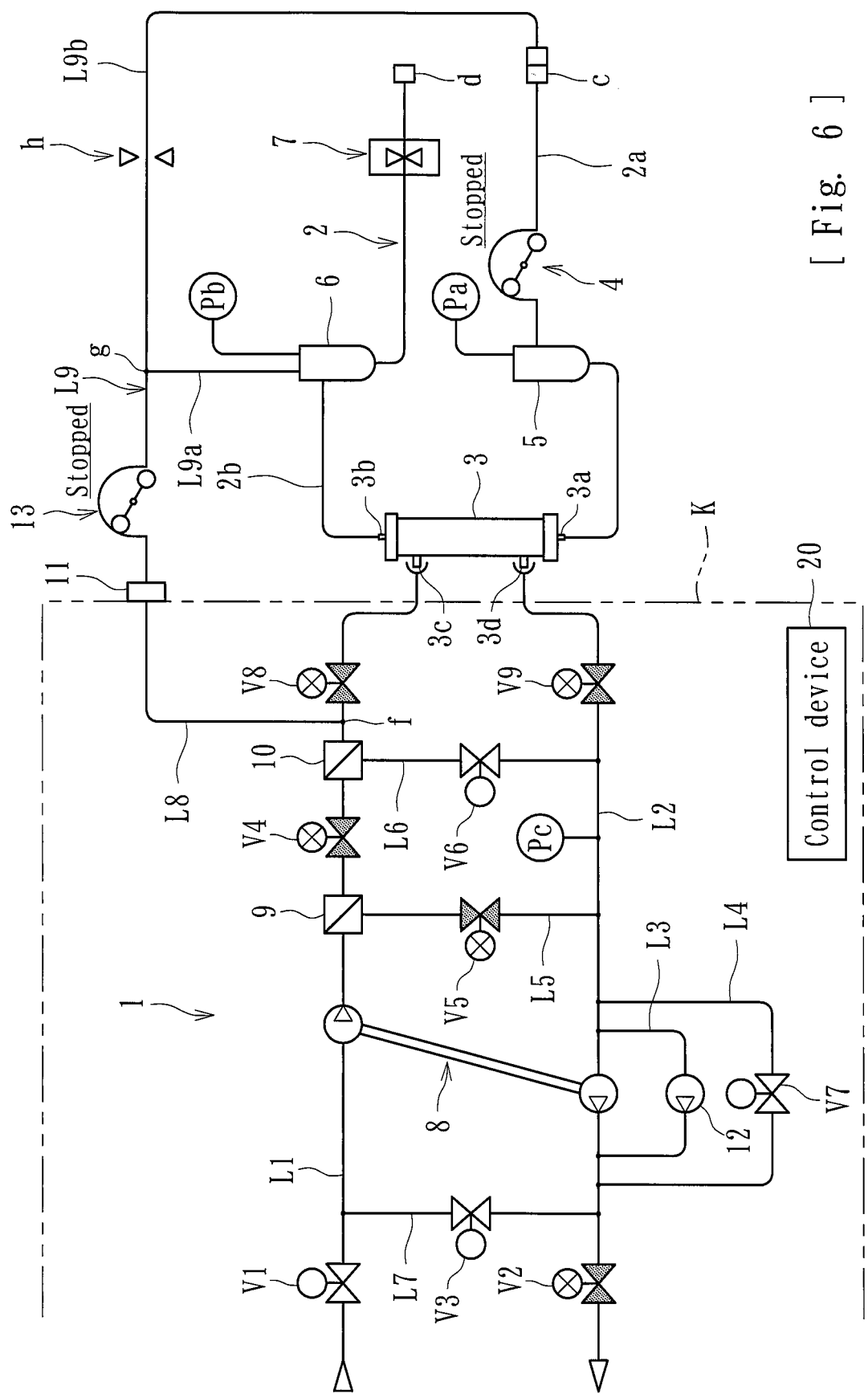
[Fig. 6]

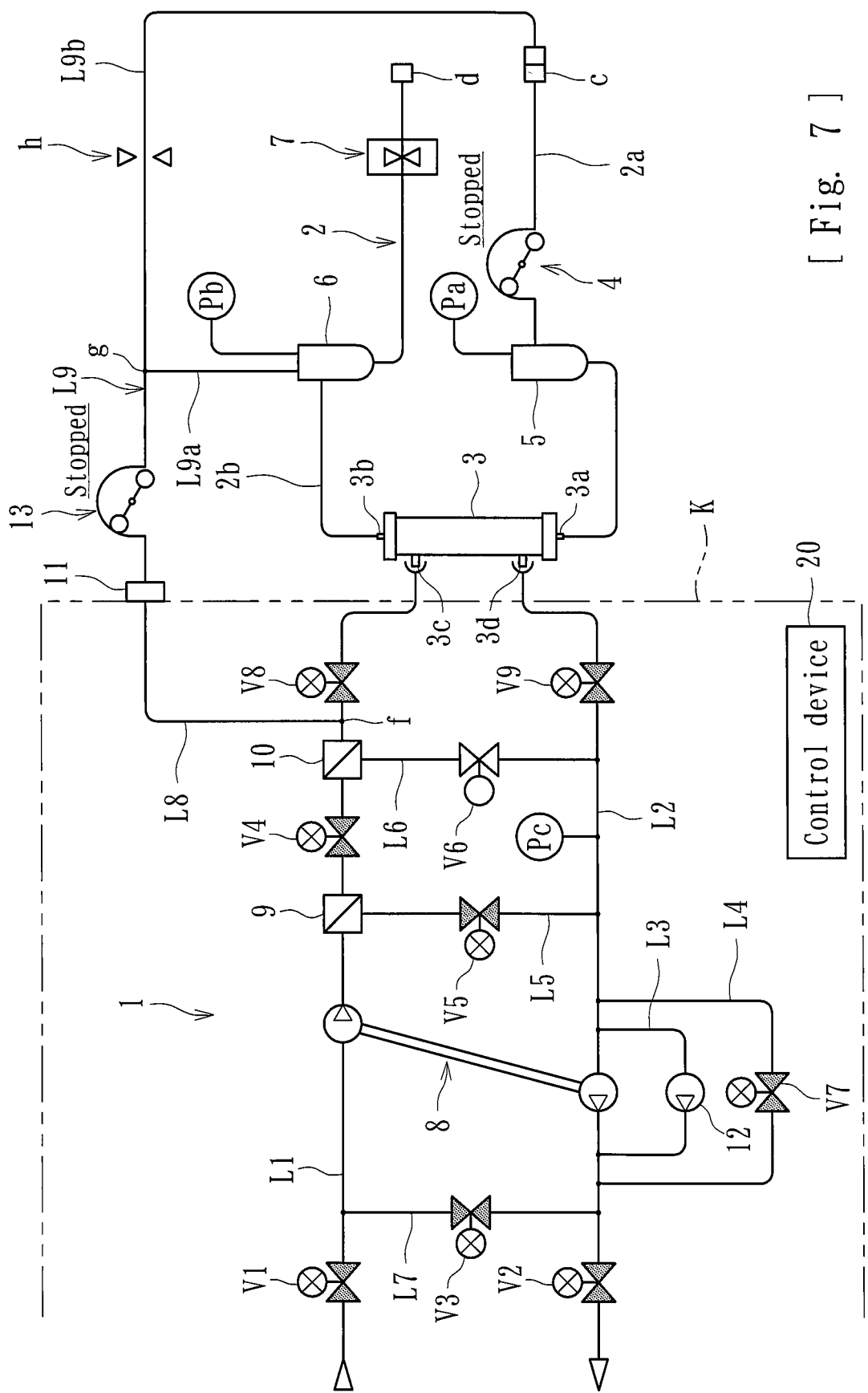
[Fig. 7]

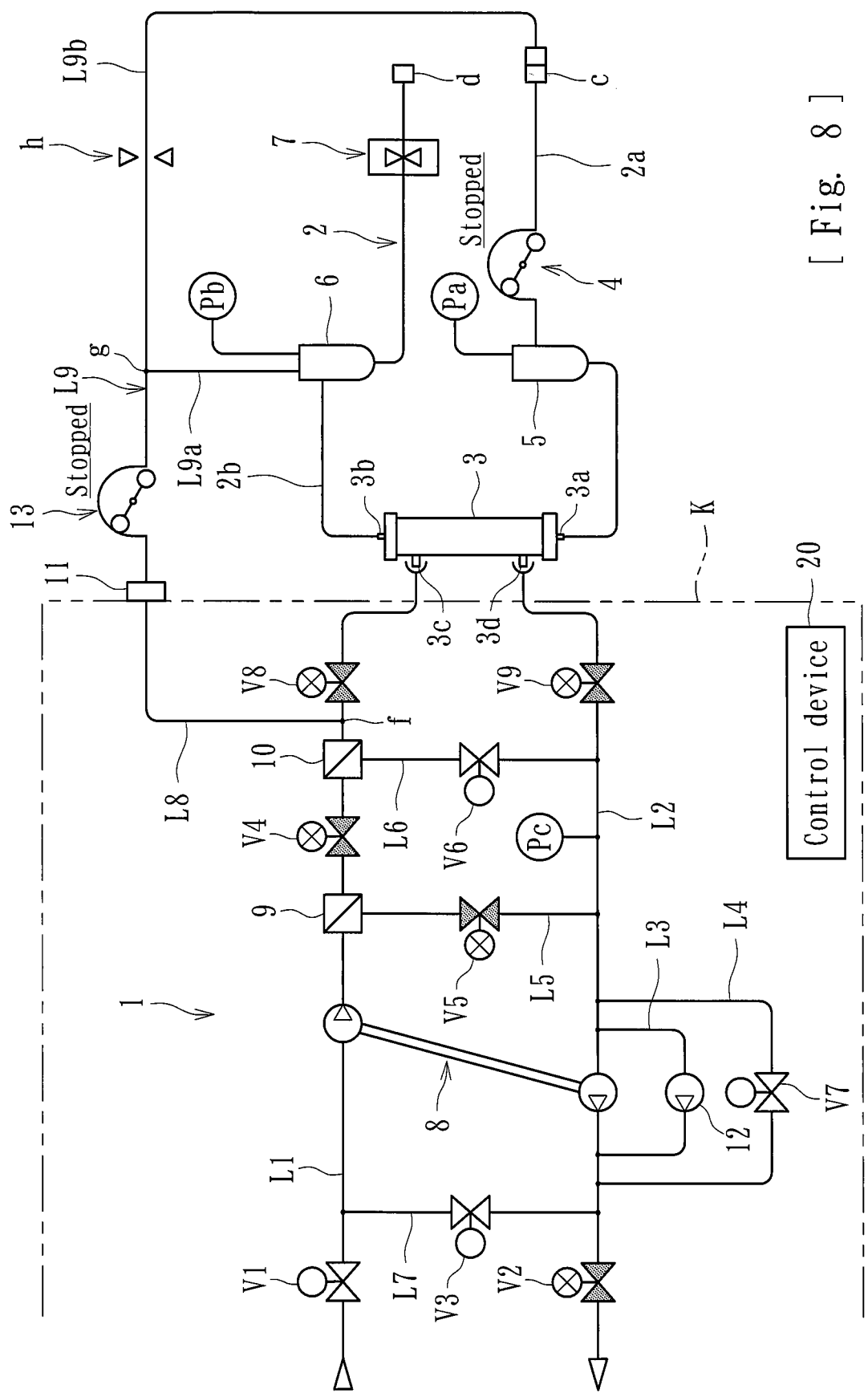
[Fig. 8]

[Fig. 9]
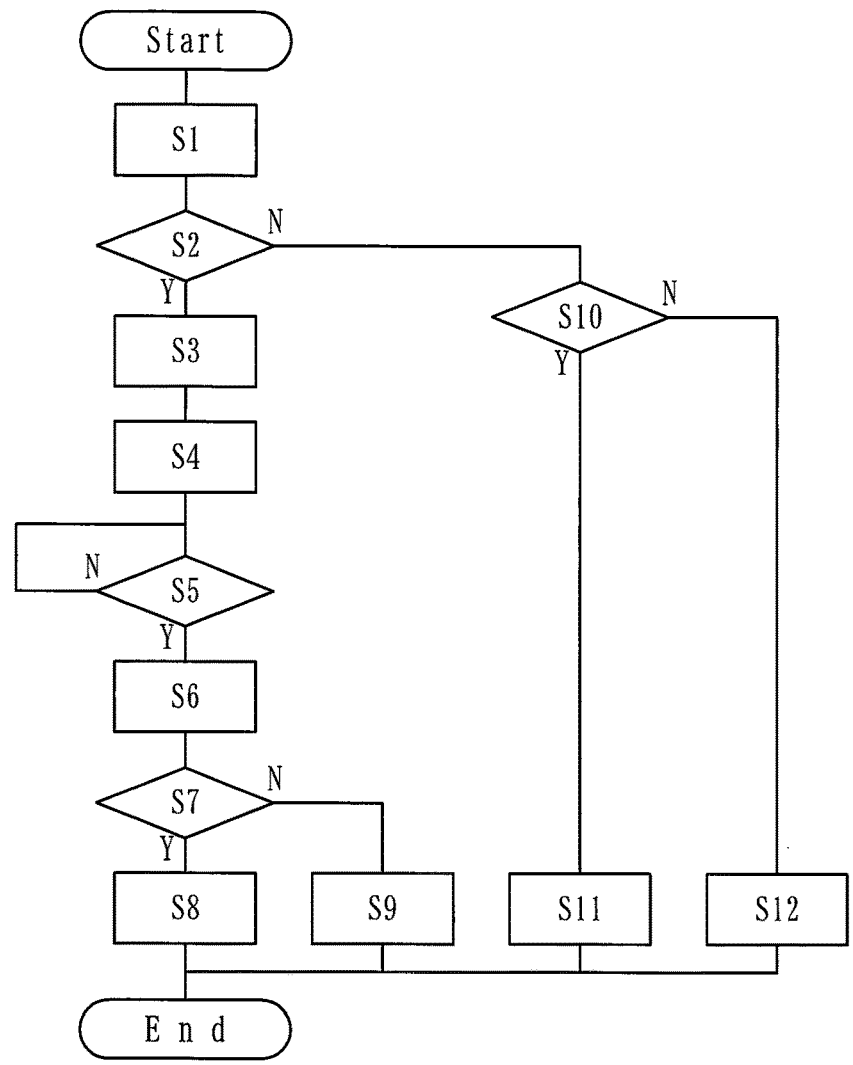
S1. Pressurize with Liquid-Feeding pressure
S2: Any pressure increase?
S3: Stop pressurization
S4: Store pressure (P0)
S5: Has predetermined time elapsed?
S6: Store pressure (P1)
S7: Is pressure retained?
S8: Release pressure
S9: Warning 1
S10: Any increase in venous pressure?
S11. Warning 2
S12: Warning 3

[ Fig. 10 ]
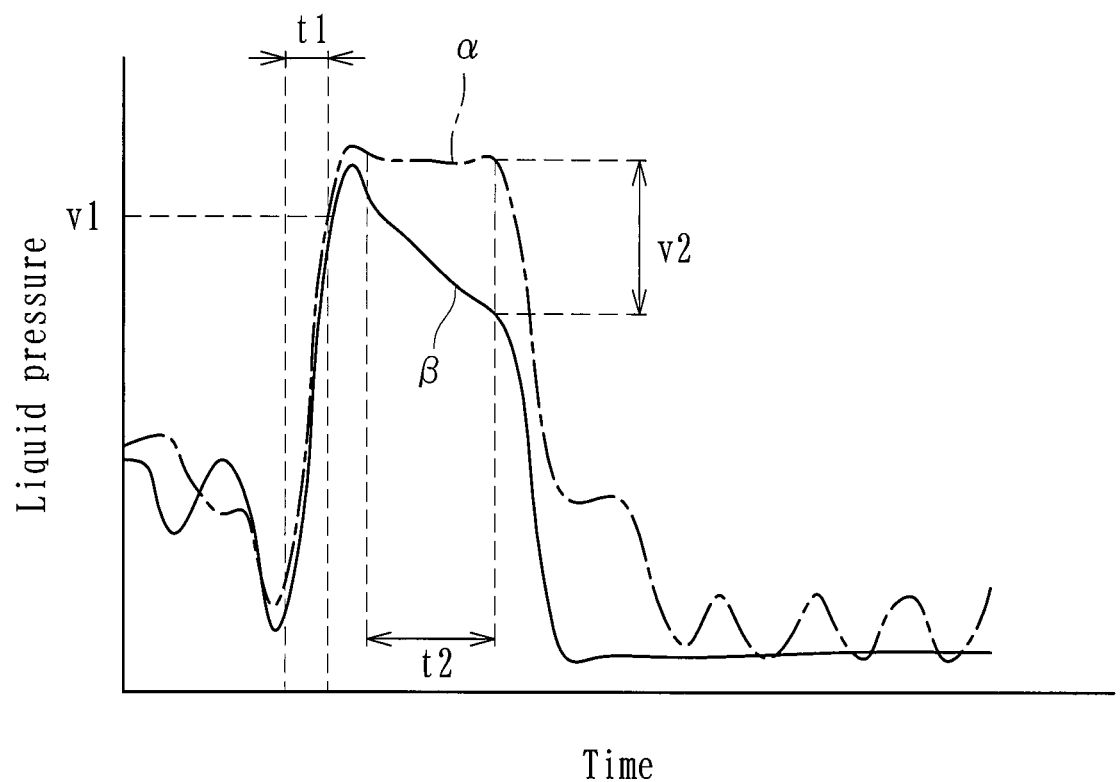

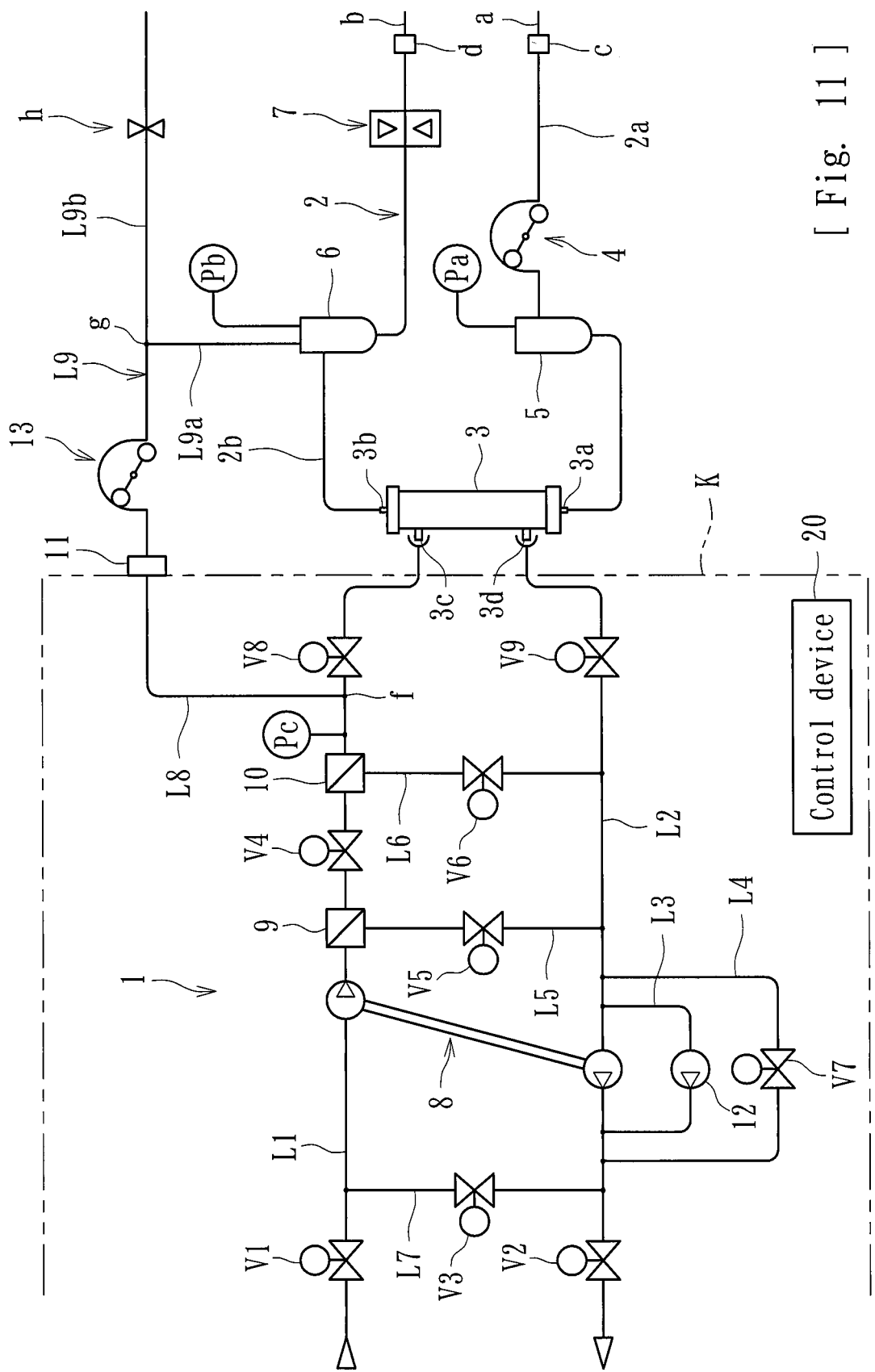
[Fig. 11]

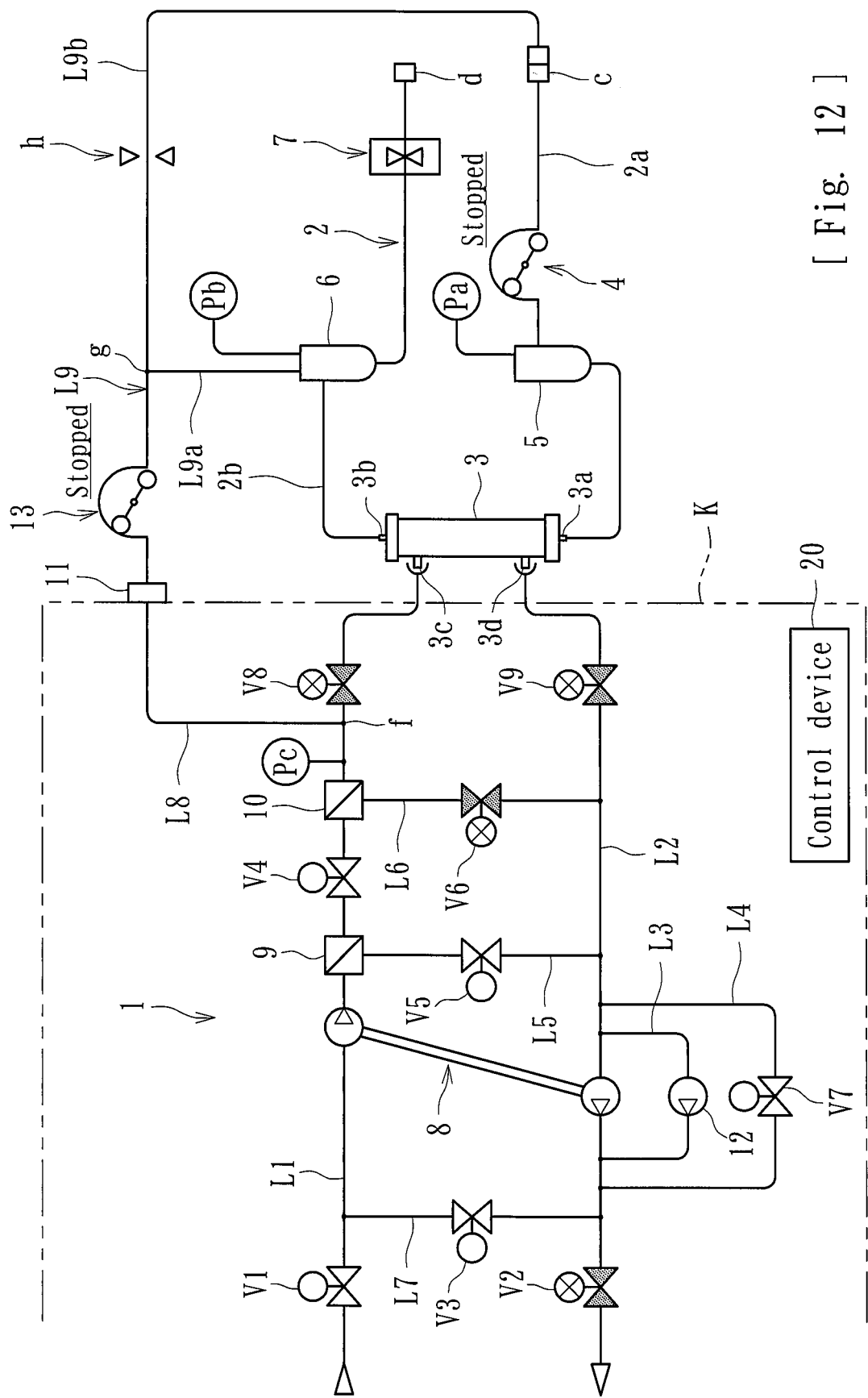
[Fig. 12]

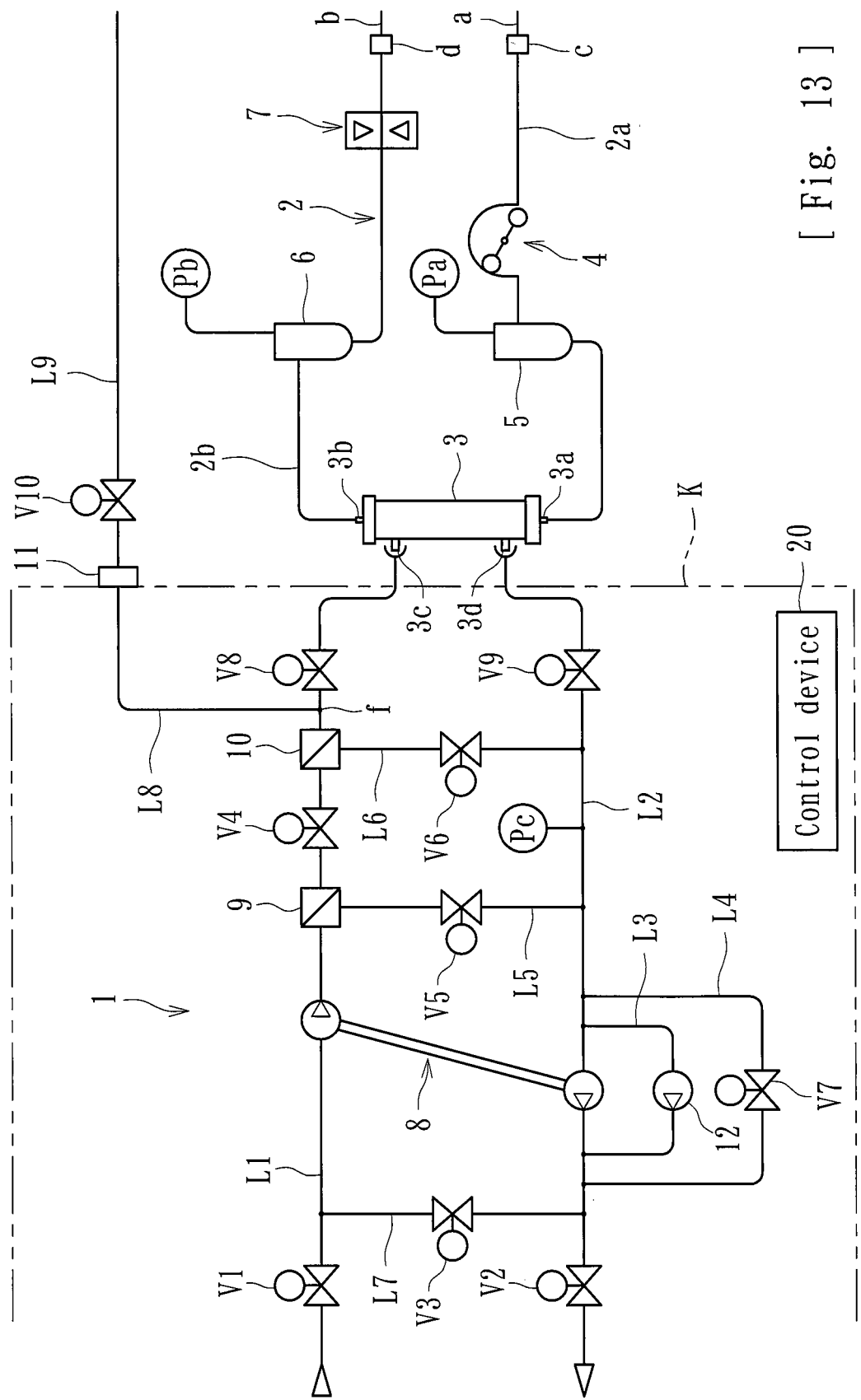
[Fig. 13]

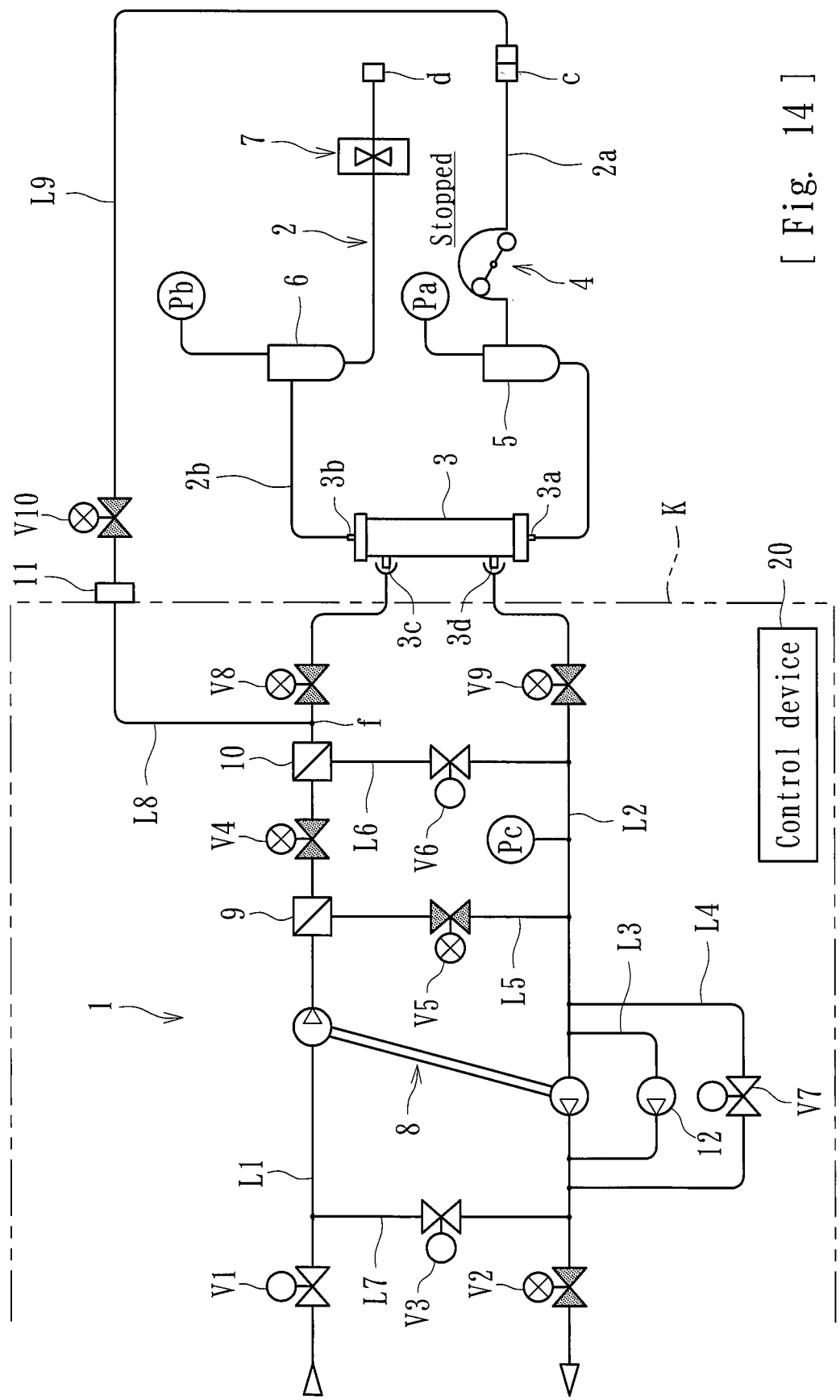
[ Fig. 14 ]

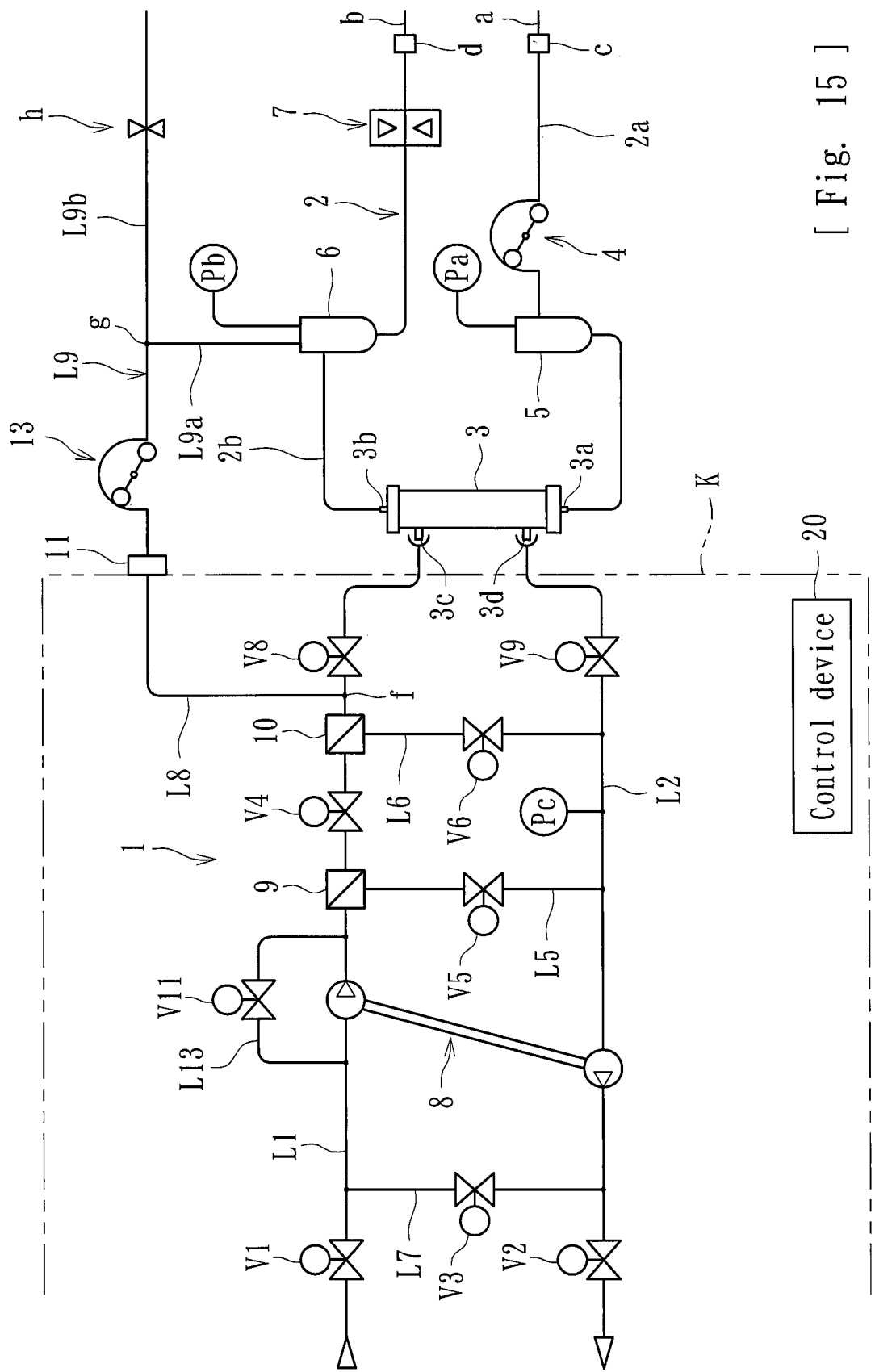
[ Fig. 15 ]

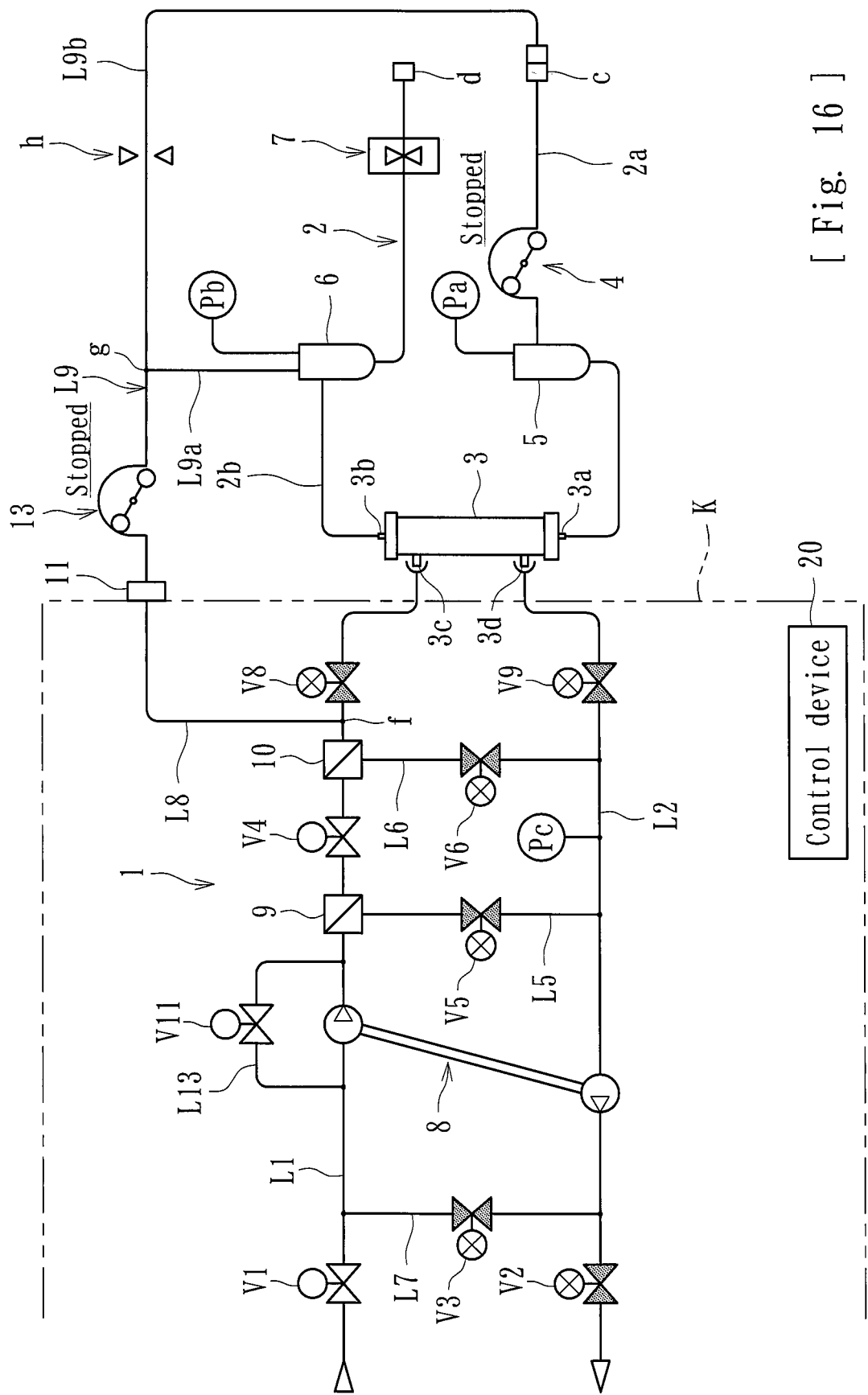
[ Fig. 16 ]

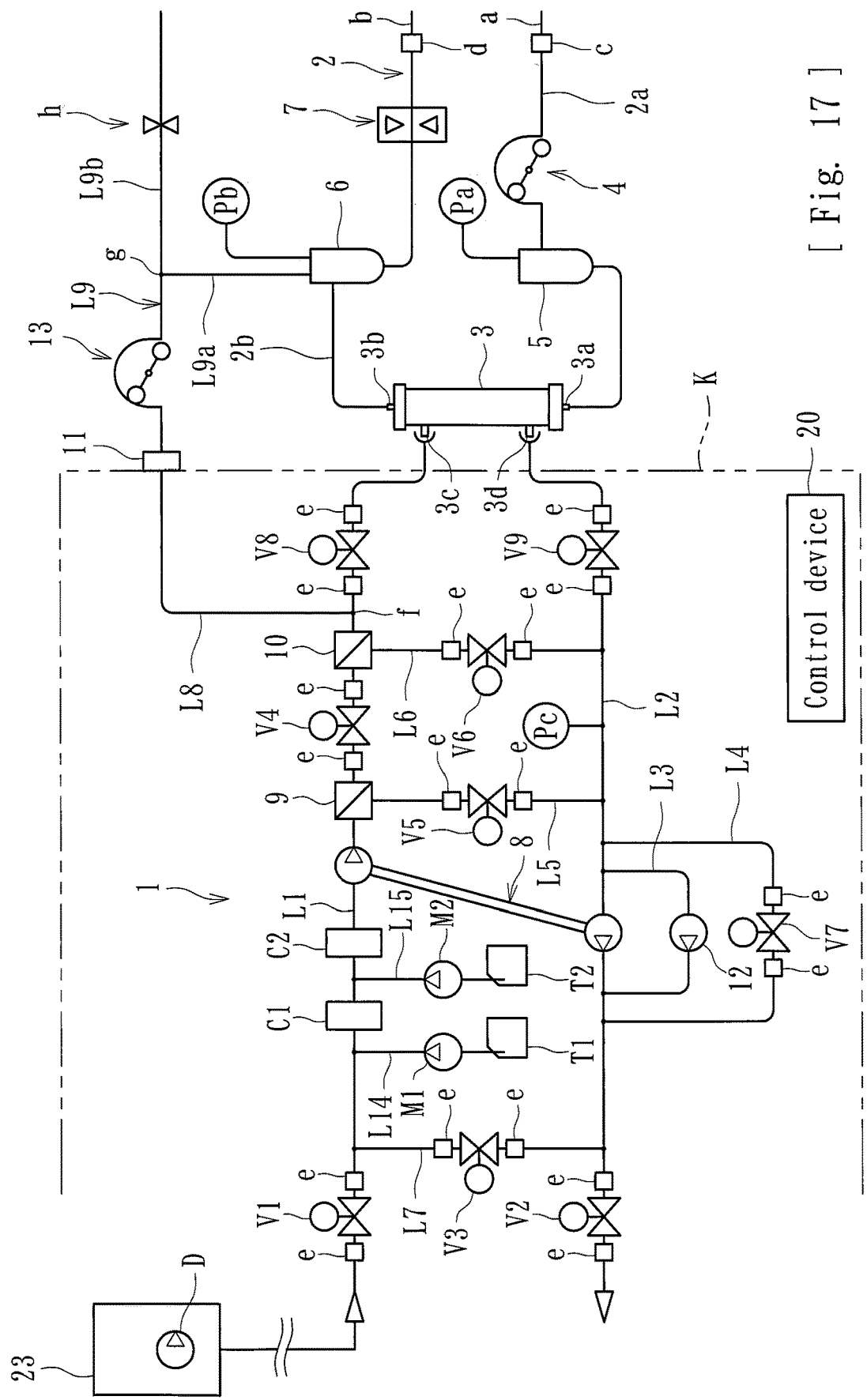
[Fig. 17]

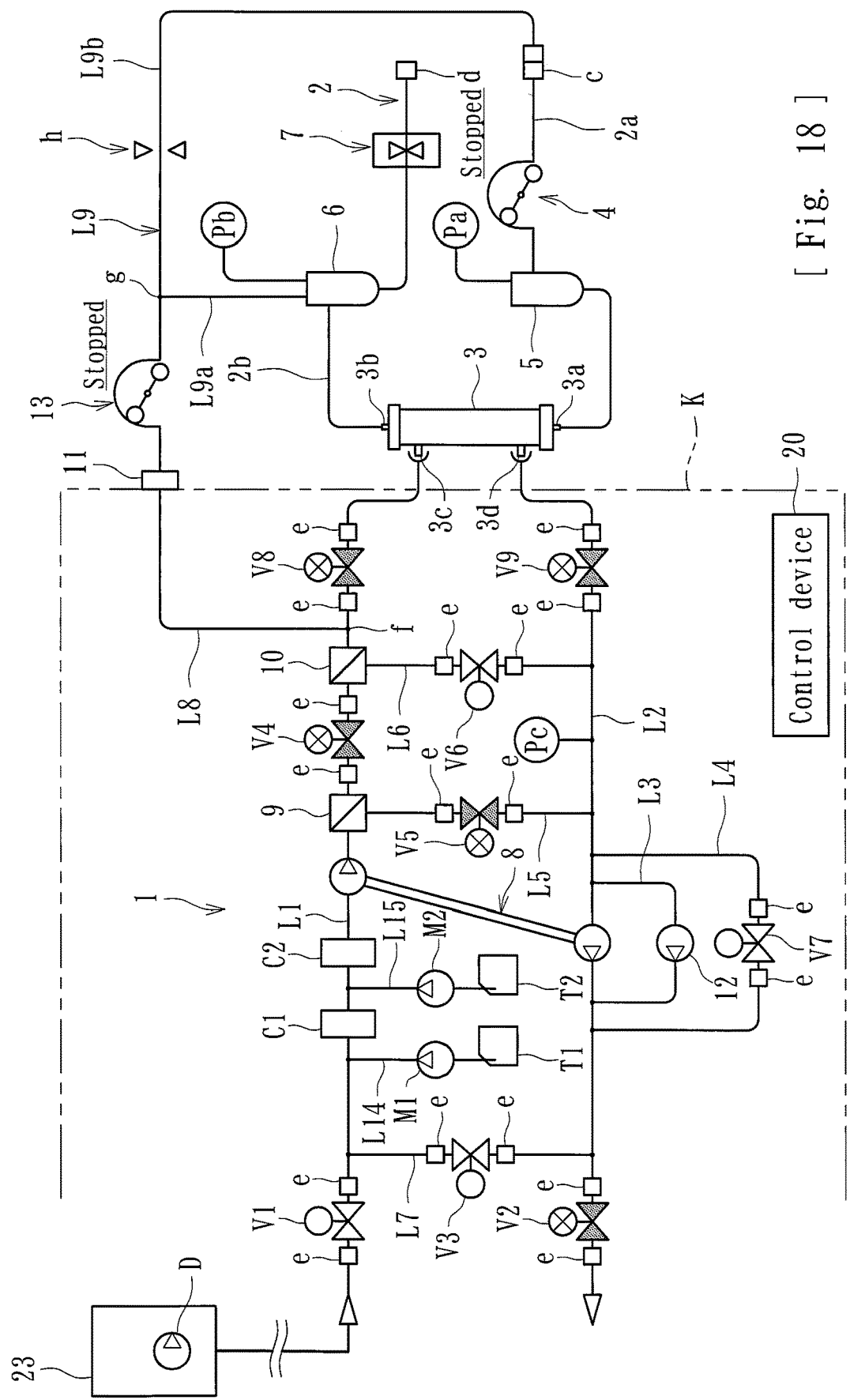
[Fig. 18]

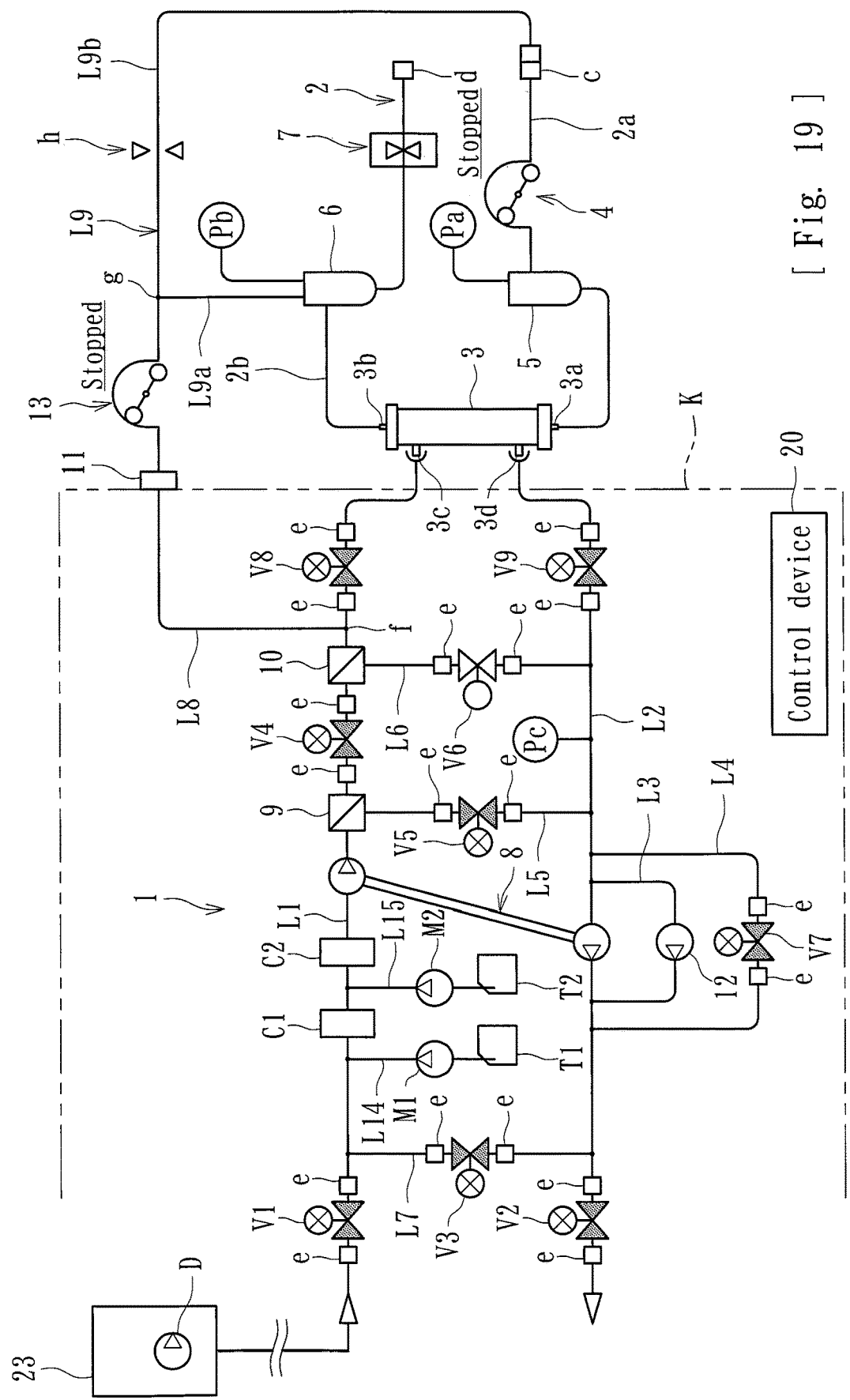
[ Fig. 19 ]

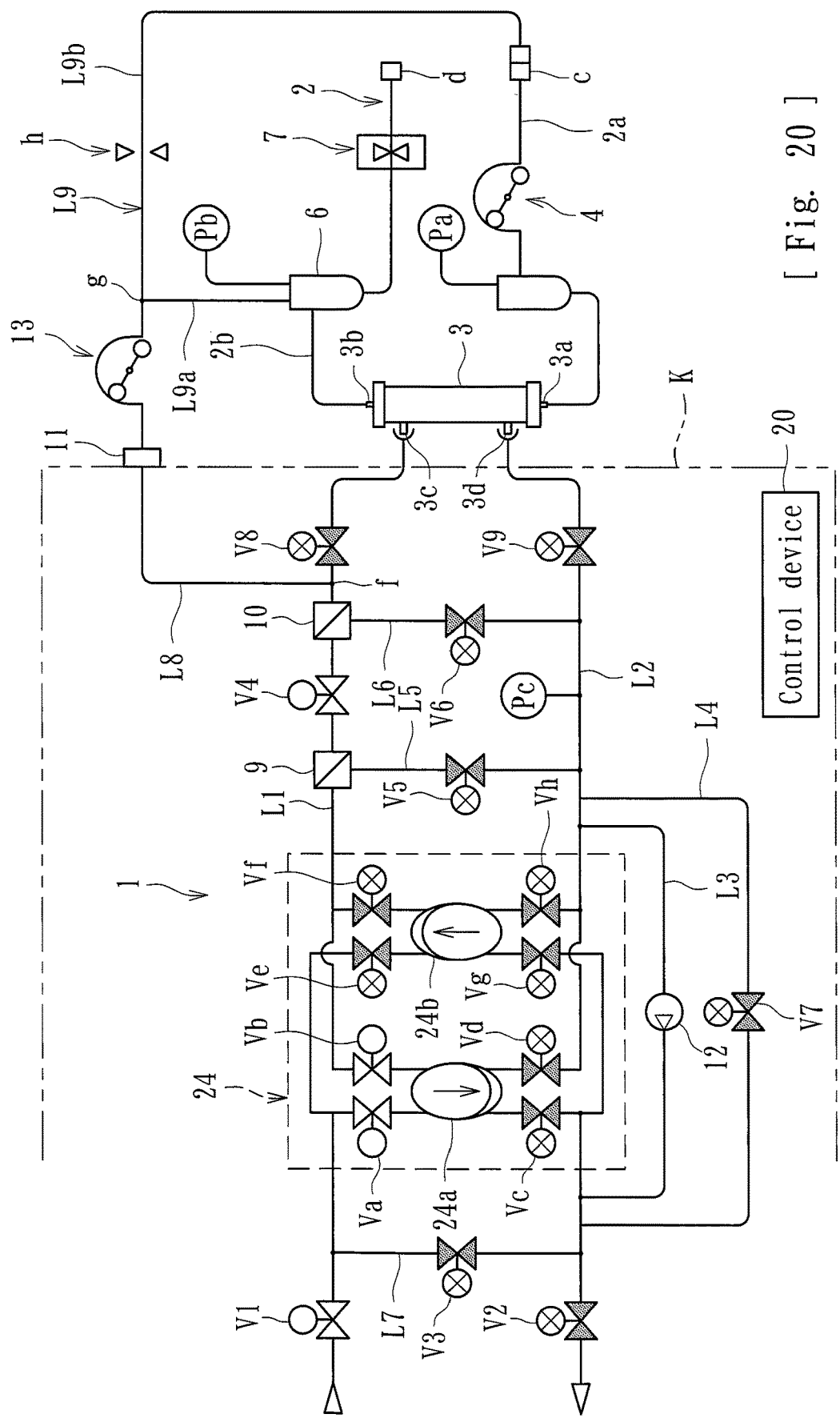
[ Fig. 20 ]

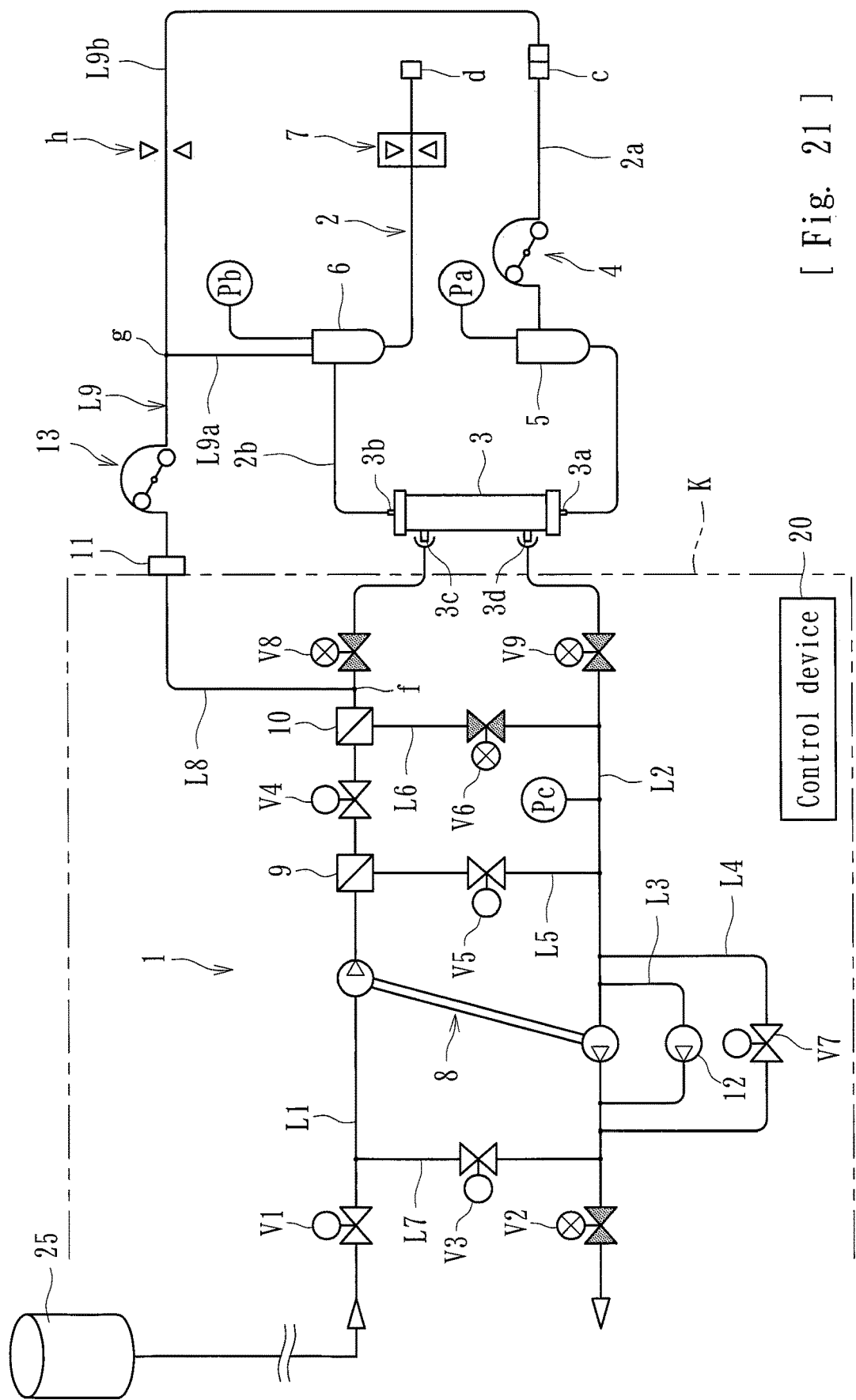
[ Fig. 21 ]

BLOOD PURIFICATION APPARATUS

FIELD

The present teachings relate to a blood purification apparatus that causes a blood purifier connected to a blood circuit to perform blood purification treatment.

BACKGROUND

For recent dialysis apparatuses serving as blood purification apparatuses, there are some technical proposals in which not only dialysis treatment (HDF or HF) but also priming, blood returning, and substitution (emergency fluid infusion) are performed with dialysate that is to be supplied to a dialyzer. In such a dialysis apparatus, the dialysate in a dialysate introduction line is supplied to a blood circuit (an arterial blood circuit or a venous blood circuit) by activating a substitution pump.

In the above dialysis apparatus, work of connecting one end of the substitution line to a collecting port provided at a predetermined position of the dialysate introduction line is necessary. Therefore, whether or not the connecting work has been done normally needs to be checked. Hence, there are some related-art proposals for dialysis apparatuses each performing a testing process in which a flow route provided with a collecting port is pressurized by activating the substitution pump or a duplex pump, and the resulting increase in the pressure or a retainment of that pressure is detected and evaluated, whereby the connection of the substitution line to the collecting port is checked (see PTL 1 and 2, for example), the teachings of which are expressly incorporated by reference herein for all purposes.

PTL 1: Japanese Unexamined Patent Application Publication No. 2011-161060

PTL 1: Japanese Unexamined Patent Application Publication No. 2012-192101

However, since the above known blood purification apparatuses each employ a displacement-type pump, such as a substitution pump or a duplex pump, for the pressurization in the testing process, the following problems arise.

A displacement-type pump is characterized in that the value of pressure increase after a specific number of revolutions or the reciprocating movements varies with the position of the rotor or the plunger and in that it takes time for the pressure to reach a predetermined value. In particular, in a peristaltic pump such as the substitution pump, the value of pressure increase or the time of pressure increase vary depending on the adjustment of the gap between the rotor and the stator. Therefore, the connection of the substitution line to the collecting port cannot be checked instantly and accurately. There is another problem in that since the substitution pump or the duplex pump is used during blood purification treatment, the testing process cannot be performed during the treatment.

SUMMARY

The present teachings have been conceived in view of the above circumstances and provides a blood purification apparatus in which the connection of a substitution line to a collecting port can be checked accurately and instantly and even during blood purification treatment.

According to the teachings herein, there is provided a blood purification apparatus including a blood circuit including an arterial blood circuit and a venous blood circuit and through which blood of a patient is allowed to extracorporeally circulate; a blood purifier connected to the blood circuit and that is capable of purifying the blood extracorporeally circulating through the blood circuit; a dialysate introduction line supplied with a predetermined liquid from a liquid-feeding device and through which a dialysate is introduced into the blood purifier, the liquid-feeding device being capable of feeding the liquid at a constant pressure; a dialysate drain line through which waste water is discharged from the blood purifier; a substitution line one end of which is connected to a collecting port provided at a predetermined position of the dialysate introduction line and an other end of which is connected to the arterial blood circuit or the venous blood circuit; a closing device provided to the substitution line and that is capable of arbitrarily closing a flow route provided by the substitution line, the closing device being configured to form, in a state where the flow route is closed, a pressure-increasing portion that includes the collecting port; and a pressure-measuring device capable of measuring a pressure in the pressure-increasing portion. The blood purification apparatus performs a testing process in which connection of the substitution line to the collecting port is checked by increasing a liquid pressure in the pressure-increasing portion and measuring the pressure with the pressure-measuring device. The testing process is performed by increasing the liquid pressure in the pressure-increasing portion by utilizing a liquid-feeding pressure applied from the liquid-feeding device.

According to the teachings herein, in the blood purification apparatus taught herein, the liquid-feeding pressure applied from the liquid-feeding device is generated with activation of a non-displacement-type pump or with a level difference.

According to the teachings herein, in the blood purification apparatus taught herein, the non-displacement-type pump is a turbo-type pump such as a centrifugal pump, an axial-flow pump, or a mixed-flow pump.

According to the teachings herein, in the blood purification apparatus taught herein, the testing process includes a first checking step of increasing the liquid pressure in the pressure-increasing portion and checking whether or not a pressure higher than or equal to a predetermined value is measured by the pressure-measuring device within a predetermined period of time, and a second checking step of checking whether or not the pressure measured by the pressure-measuring device is retained for a predetermined period of time after the increase of the liquid pressure in the pressure-increasing portion is stopped.

According to the teachings herein, in the blood purification apparatus taught herein, the venous blood circuit is provided with a venous-pressure sensor that is capable of detecting, during blood purification treatment, a venous pressure of the blood that is under extracorporeal circulation. The testing process further includes a third checking step in which if it is determined in the first checking step that the pressure higher than or equal to the predetermined value is not measured within the predetermined period of time, whether or not there is an increase in the pressure detected by the venous-pressure sensor is checked.

According to the teachings herein, in the blood purification apparatus taught herein, the dialysate introduction line is supplied with clean water from the liquid-feeding device and with undiluted dialysate, the clean water and the undiluted dialysate being mixed together into the dialysate that is to be introduced into the blood purifier. The dialysate introduction line is provided with an electrical-continuity sensor that is capable of identifying which of the clean water and the dialysate is present by checking whether or not there is electrical continuity at an application of a voltage. If what is identified is the clean water, a washing process in which the dialysate introduction line is washed with the clean water is performed.

According to the teachings herein, in the blood purification apparatus taught herein, the electrical-continuity sensor is provided to a valve device that is capable of opening and closing the flow route of the liquid, and the electrical-continuity sensor is capable of detecting an open or closed state of the valve device by checking whether or not there is electrical continuity at the application of the voltage.

According to the teachings herein, the testing process is performed by increasing the liquid pressure in the pressure-increasing portion by utilizing a liquid-feeding pressure applied from the liquid-feeding device that is capable of feeding the liquid at a constant pressure. Therefore, the process of checking the connection of the substitution line to the collecting port can be performed accurately and instantly and during blood purification treatment.

According to the teachings herein, the testing process is performed by increasing the liquid pressure in the pressure-increasing portion by utilizing the liquid-feeding pressure generated by activating the non-displacement-type pump that is a turbo-type pump such as a centrifugal pump, an axial-flow pump, or a mixed-flow pump; or by utilizing the liquid-feeding pressure generated by the level difference. Therefore, the liquid-feeding pressure for increasing the liquid pressure in the pressure-increasing portion can be obtained with a general-purpose device.

According to the teachings herein, the testing process includes the first checking step of increasing the liquid pressure in the pressure-increasing portion and checking whether or not the pressure higher than or equal to the predetermined value is measured by the pressure-measuring device within the predetermined period of time, and the second checking step of checking whether or not the pressure measured by the pressure-measuring device is retained for the predetermined period of time after the increase of the liquid pressure in the pressure-increasing portion is stopped. Therefore, whether or not the pressure-increasing portion is formed normally can be checked in the first checking step, and whether or not the connection of the substitution line to the collecting port is normal can be checked in the second checking step.

According to the teachings herein, the testing process further includes the third checking step in which if it is determined in the first checking step that the pressure higher than or equal to the predetermined value is not measured within the predetermined period of time, whether or not there is an increase in the pressure detected by the venous-pressure sensor is checked. Therefore, whether or not the closing by the closing device is performed normally can be checked by utilizing the venous-pressure sensor.

According to the teachings herein, the dialysate introduction line is supplied with the clean water from the liquid-feeding device and with the undiluted dialysate, the clean water and the undiluted dialysate being mixed together into the dialysate that is to be introduced into the blood purifier. The dialysate introduction line is provided with an electrical-continuity sensor that is capable of identifying which of the clean water and the dialysate is present by checking whether or not there is electrical continuity at an application of a voltage. If what is identified is the clean water, the washing process in which the dialysate introduction line is washed with the clean water is performed. Therefore, in a so-called personal apparatus, the entry of clean water into the dialysate introduction line can be recognized through the testing process, and the washing process can be performed automatically.

According to the teachings herein, the electrical-continuity sensor is provided to the valve device that is capable of opening and closing the flow route of the liquid, and the electrical-continuity sensor is capable of detecting the open or closed state of the valve device by checking whether or not there is electrical continuity at the application of the voltage. Therefore, the electrical-continuity sensor can have both the function of detecting the open/closed state of the valve device and the function of recognizing the entry of clean water into the dialysate introduction line.

BRIEF DESCRIPTION OF THE DRAWINGS

FIG. 1 is a schematic diagram illustrating the entirety of a blood purification system including blood purification apparatuses each according to a first embodiment of the present teachings.

FIG. 2 is a schematic diagram of the blood purification apparatus.

FIG. 3 is a schematic sectional view of a collecting port included in the blood purification apparatus.

FIG. 4 is a schematic sectional view of the collecting port with a substitution line connected thereto.

FIG. 5 is a schematic diagram of the blood purification apparatus in a state for performing priming.

FIG. 6 is a schematic diagram of the blood purification apparatus in a state for performing a testing process (a first checking step).

FIG. 7 is a schematic diagram of the blood purification apparatus in another state for performing the testing process (a second checking step).

FIG. 8 is a schematic diagram of the blood purification apparatus in yet another state for performing the testing process (a third checking step).

FIG. 9 is a flow chart of a control operation for the testing process that is performed in the blood purification apparatus.

FIG. 10 is a graph illustrating the results of measurements performed by a pressure-measuring device during the testing process.

FIG. 11 is a schematic diagram illustrating a case of the first embodiment in which the pressure-measuring device is provided at a different position.

FIG. 12 is a schematic diagram illustrating a state for performing the testing process (the first checking step) in the same case.

FIG. 13 is a schematic diagram illustrating another case of the first embodiment in which an electromagnetic valve is provided in replacement of a substitution pump.

FIG. 14 is a schematic diagram illustrating a state for performing the testing process (the first checking step) in the same case.

FIG. 15 is a schematic diagram illustrating yet another case of the first embodiment in which a line for detouring a duplex pump is added.

FIG. 16 is a schematic diagram illustrating a state of performing the testing process (the first checking step) in the same case.

FIG. 17 is a schematic diagram of a blood purification apparatus according to a second embodiment of the present teachings.

FIG. 18 is a schematic diagram of the blood purification apparatus in a state for performing the testing process (the first checking step).

FIG. 19 is a schematic diagram of the blood purification apparatus in another state for performing the testing process (the second checking step).

FIG. 20 is a schematic diagram of a blood purification apparatus according to another embodiment of the present teachings.

FIG. 21 is a schematic diagram of a blood purification apparatus according to yet another embodiment of the present teachings.

DETAILED DESCRIPTION

The present teachings will now be described specifically with reference to the drawings.

As illustrated in FIG. 1, a blood purification apparatus according to an embodiment is applied to each of a plurality of hemodialysis apparatuses 1 (monitoring apparatuses for dialysis) installed in a dialysis room (A) (a treatment room) provided at a medical site such as a hospital and is included in a blood purification system, which also includes a dialysate-supplying apparatus 21, a dissolving apparatus 22, and a water treatment apparatus 23 that are installed in a machine room (B) provided at the medical site but separate from the dialysis room (A).

The water treatment apparatus 23 includes a module (a purification-and-filtration device) having thereinside filtration membranes or the like so as to obtain clean water (RO water) by purifying raw water. The water treatment apparatus 23 is connected to the dissolving apparatus 22 with a tube L12, thereby being capable of supplying the clean water to the dissolving apparatus 22. The water treatment apparatus 23 is further connected to the dialysate-supplying apparatus 21 with tubes L10 and L11, thereby being capable of supplying the clean water to the dialysate-supplying apparatus 21. The clean water obtained in the water treatment apparatus 23 is used for preparing a dialysate in the dialysate-supplying apparatus 21, or is used as washing water for washing the dialysate-supplying apparatus 21, tubes provided to the hemodialysis apparatuses 1, and so forth.

The dissolving apparatus 22 is supplied with, for example, a predetermined amount of powder medicine for dialysis. The powder medicine for dialysis and the clean water supplied from the water treatment apparatus 23 are mixed together, whereby undiluted dialysate having a predetermined concentration is prepared in the dissolving apparatus 22. The dissolving apparatus 22 is connected to the dialysate-supplying apparatus 21 with the tube L10 and is therefore capable of supplying the thus prepared undiluted dialysate to the dialysate-supplying apparatus 21.

The dialysate-supplying apparatus 21 is capable of preparing a dialysate having a predetermined concentration from the clean water obtained by the water treatment apparatus 23 and the undiluted dialysate prepared by the dissolving apparatus 22. The dialysate-supplying apparatus 21 is connected to each of a plurality of hemodialysis apparatuses 1 (the blood purification apparatuses) with a tube L1a, thereby being capable of supplying the dialysate having a predetermined concentration to each of the hemodialysis apparatuses 1. Specifically, the dialysate-supplying apparatus 21 according to the present embodiment includes a liquid-feeding device (D) that is capable of supplying a predetermined liquid (the dialysate having a predetermined concentration that is prepared by the dialysate-supplying apparatus 21) with a constant pressure. When the liquid-feeding device (D) is activated, the predetermined liquid, such as the dialysate or the clean water serving as washing water, can be supplied to each of the hemodialysis apparatuses 1 through the tube L1a.

The liquid-feeding device (D) is a non-displacement-type pump that is a turbo-type pump or the like such as a centrifugal pump, an axial-flow pump, or a mixed-flow pump. In general, the non-displacement-type pump (a turbo-type pump) refers to a pump configured to supply energy to liquid by causing, when activated, an impeller to rotate in a casing, and is a general term representing a centrifugal pump, a mixed-flow pump, an axial-flow pump, and the like. Such a non-displacement-type pump causes no pressure changes, unlike a displacement-type pump in which the pressure changes during a period of rotation of the rotor or reciprocating movement of the plunger thereof. Therefore, a continuous flow can be obtained.

Referring now to FIG. 2, each hemodialysis apparatus 1 according to the present embodiment includes a blood circuit 2, a dialyzer 3 (a blood purifier), a blood pump 4, an arterial air-trap chamber 5, a venous air-trap chamber 6, a clamping device 7, a duplex pump 8, filtration filters (9 and 10), a collecting port 11, an ultrafiltration pump 12, a substitution pump 13 (a closing device), a dialysate introduction line L1, a dialysate drain line L2, a substitution line L9, a pressure-measuring device Pc, and a control device 20. In addition, reference numeral K denotes an apparatus body, in which tubes such as the dialysate introduction line L1 and the dialysate drain line L2, and actuators such as the duplex pump 8, the ultrafiltration pump 12, and the blood pump 4 are provided.

The blood circuit 2 includes an arterial blood circuit 2a and a venous blood circuit 2b and is made of a flexible tube through which blood of a patient is allowed to extracorporeally circulate. The arterial blood circuit 2a is connected at the distal end thereof to an arterial puncture needle a with a connector c interposed therebetween, and is provided at a halfway position thereof with the arterial air-trap chamber 5, where the liquid flowing through the arterial blood circuit 2a can undergo bubble removal. The arterial air-trap chamber 5 provided to the arterial blood circuit 2a is connected to an inlet-pressure sensor Pa that is capable of detecting the inlet pressure of the dialyzer 3.

The arterial blood circuit 2a is further provided with the blood pump 4 between the connector c and the arterial air-trap chamber 5. The blood pump 4 is a peristaltic pump (a displacement-type pump). In the blood pump 4, a squeezable portion of the flexible tube is squeezed in the lengthwise direction by a roller with the rotation of a rotor, whereby the liquid in the arterial blood circuit 2a can be delivered toward the dialyzer 3.

The venous blood circuit 2b is connected at the distal end thereof to a venous puncture needle (b) with a connector (d) interposed therebetween, and is provided at a halfway position thereof with the venous air-trap chamber 6, where the liquid flowing in the venous blood circuit 2b can undergo bubble removal. The venous air-trap chamber 6 provided to the venous blood circuit 2b is connected to a venous-pressure sensor Pb that is capable of detecting the venous pressure of the blood that is extracorporeally circulated during the blood purification treatment.

The venous blood circuit 2b is further provided with the clamping device 7 between the connector d and the venous air-trap chamber 6. The clamping device 7 includes a push rod or the like with which a flow route provided by the venous blood circuit 2b is closable arbitrarily. For example, if the presence of bubbles in the blood is detected by a bubble-checking device, which is not illustrated, the flow route is closed so that bubbles can be prevented from entering the body of the patient.

When the blood pump 4 is activated with the arterial puncture needle a and the venous puncture needle b being stuck in the patient, the blood of the patient flows through the arterial blood circuit 2a while undergoing bubble removal in the arterial air-trap chamber 5 and reaches the dialyzer 3, where the blood is purified. Then, the purified blood flows through the venous blood circuit 2b while undergoing bubble removal in the venous air-trap chamber 6 and returns into the body of the patient. Thus, the blood of the patient is purified by the dialyzer 3 while being extracorporeally circulated through the blood circuit from the distal end of the arterial blood circuit 2a to the distal end of the venous blood circuit 2b.

The dialyzer 3 has, in a housing thereof, a blood inlet 3a (a blood introduction port), a blood outlet 3b (a blood delivery port), a dialysate inlet 3c (an inlet of a dialysate flow route, or a dialysate introduction port), and a dialysate outlet 3d (an outlet of the dialysate flow route, or a dialysate delivery port). The proximal end of the arterial blood circuit 2a is connected to the blood inlet 3a. The proximal end of the venous blood circuit 2b is connected to the blood outlet 3b. The dialysate inlet 3c and the dialysate outlet 3d are connected to the dialysate introduction line L1 and the dialysate drain line L2, respectively, extending from the apparatus body (K).

The dialyzer 3 houses a plurality of hollow fibers (not illustrated), and the hollow fibers serve as blood purification membranes for purifying the blood. The blood purification membranes in the dialyzer 3 define blood flow routes (spaces inside the respective hollow fibers and each extending between the blood inlet 3a and the blood outlet 3b) in which the blood of the patient flows and dialysate flow routes (spaces outside the hollow fibers and each extending between the dialysate inlet 3c and the dialysate outlet 3d) in which the dialysate flows.

That is, the dialyzer 3 has the blood inlet 3a that allows the blood to be introduced into the blood flow routes, the blood outlet 3b that allows the blood to be discharged from the blood flow routes, the dialysate inlet 3c that allows the dialysate to be introduced into the dialysate flow routes, and the dialysate outlet 3d that allows the dialysate to be discharged from the dialysate flow routes. The dialyzer 3 is configured such that the direction in which the blood flows from the blood inlet 3a toward the blood outlet 3b and the direction in which the dialysate flows from the dialysate inlet 3c toward the dialysate outlet 3d are opposite to each other. The hollow fibers serving as the blood purification membranes each have a number of very small holes (pores) extending therethrough from the outer peripheral surface to the inner peripheral surface. Hence, impurities and the like contained in the blood are allowed to penetrate through the membranes into the dialysate.

As described above, the dialysate inlet 3c and the dialysate outlet 3d of the dialyzer 3 are connected to the dialysate introduction line L1 and the dialysate drain line L2, respectively. The dialysate having a predetermined concentration is allowed to be introduced into the dialyzer 3 through the dialysate introduction line L1, whereas waste water from the dialyzer 3 is allowed to be discharged through the dialysate drain line L2. The proximal end of the dialysate introduction line L1 is connected to the tube L1a illustrated in FIG. 1, and the dialysate having a predetermined concentration can be supplied thereinto from the liquid-feeding device D. On the other hand, the proximal end of the dialysate drain line L2 is connected to a waste-liquid container or the like through a tube, which is not illustrated.

The dialysate introduction line L1 is provided with electromagnetic valves V1, V4, and V8. By opening or closing the electromagnetic valves, the flow route can be closed or opened arbitrarily. The dialysate drain line L2 is provided with electromagnetic valves V2 and V9. By opening or closing the electromagnetic valves, the flow route can be opened or closed arbitrarily. A bypass line L7 forms a flow route connecting the dialysate introduction line L1 and the dialysate drain line L2 to each other, and is provided with an electromagnetic valve V3 at a halfway position thereof.

The duplex pump 8 is provided over the dialysate introduction line L1 and the dialysate drain line L2. The duplex pump 8 is a displacement-type pump for suppling the dialysate having a predetermined concentration fed from the liquid-feeding device (D) to the dialyzer 3 while discharging the waste water from the dialyzer 3. On the other hand, the dialysate drain line L2 is provided with detour lines L3 and L4 that detour the duplex pump 8. The detour line L3 is provided with the ultrafiltration pump 12 for removing water from the blood of the patient flowing through the dialyzer 3. The detour line L4 is provided with an electromagnetic valve V7.

The dialysate introduction line L1 is further provided with the filtration filters 9 and 10 between the duplex pump 8 and the dialyzer 3. The filtration filters 9 and 10 are provided for filtering and purifying the dialysate flowing in the dialysate introduction line L1. Bypass lines L5 and L6 extend from the filtration filters 9 and 10, respectively, and are connected to the dialysate drain line L2 so as to introduce the dialysate thereinto. The bypass lines L5 and L6 are provided at halfway positions thereof with electromagnetic valves V5 and V6, respectively.

The pressure-measuring device Pc is a pressure sensor provided to the dialysate drain line L2 between the connection to the bypass line L5 and the connection to the bypass line L6. The pressure-measuring device Pc is capable of measuring in real time the liquid pressure in a pressure-increasing portion, which is formed in a testing process to be described below, and transmitting the measured value to the control device 20. Note that a plurality of pressure sensors that are capable of measuring the liquid pressure may be provided at different positions, respectively.

The substitution line L9 forms a flow route connected at one end thereof to the collecting port 11 provided at a predetermined position of the dialysate introduction line L1 (in the present embodiment, at the distal end of a branch line L8 branching off from a branch point f of the dialysate introduction line L1) and at the other end thereof to the venous air-trap chamber 6 provided to the venous blood circuit 2b (or to the arterial air-trap chamber 5). The other end of the substitution line L9 according to the present embodiment branches into two at a branch point (g). The end of one branch line L9a is connected to the venous air-trap chamber 6 (or to the arterial air-trap chamber 5). The end of the other branch line L9b is connectable to the connector c at the distal end of the arterial blood circuit 2a (see FIG. 5). The flow route provided by the branch line L9b included in the substitution line L9 is arbitrarily openable and closable with a clamping device h such as a pair of forceps. The substitution line L9 is provided with the substitution pump 13 on the upstream side thereof with respect to the branch point (g). When the substitution pump 13 is driven to rotate, the liquid in the dialysate introduction line L1 can be introduced into the blood circuit 2 (in the present embodiment, the venous blood circuit 2b).

In particular, the substitution pump 13 according to the present embodiment is configured as a peristaltic pump, as with the blood pump 4. The substitution pump 13 serves as a closing device that is capable of arbitrarily closing the flow route of the substitution line L9 when the substitution pump 13 is stopped, and is configured to form a pressure-increasing portion including the collecting port 11 when the flow route is closed. The collecting port 11 is a port provided in the apparatus body (K) and is openable and closable by a lid member 18 that is turnable about a shaft 14 as illustrated in FIG. 3. Specifically, the lid member 18 is turnable between a closing position where the lid member 18 covers the collecting port 11 and an opening position where the lid member 18 allows the collecting port 11 to be exposed to the outside. When the lid member 18 is at the closing position, the lid member 18 can close the open end of the collecting port 11 with the urging force exerted by a spring 15.

When the lid member 18 that is at the closing position is moved toward the right side in the drawing against the urging force of the spring 15 and is turned about the shaft 14, the lid member 18 having been at the closing position can be moved to the opening position. In that state, one end of the substitution line L9 is connected to the collecting port 11 as illustrated in FIG. 4. The one end of the substitution line L9 is provided with a connector member 19 as illustrated in the drawing. When an internal screw portion provided in the connector member 19 is screwed onto an external screw portion provided on the collecting port 11 with the one end of the substitution line L9 fitted in the collecting port 11, the collecting port 11 and the one end of the substitution line L9 can be tightly connected to each other.

The lid member 18 is provided at a predetermined position thereof with a magnet 16 that is capable of generating magnetic force. The lid member 18 is further provided with a reed switch 17 that is capable of generating an electrical on/off-signal when detecting the magnetic force. The reed switch 17 is provided at a position that faces the magnet 16 when the lid member 18 is at the closing position. Hence, whether the lid member 18 is at the closing position or the opening position can be detected on the basis of the on-signal or the off-signal generated by the reed switch 17.

The control device 20 is a microcomputer or the like, for example, that is capable of controlling the opening and closing of the electromagnetic valves V1 to V9 and the clamping device 7 included in the hemodialysis apparatus 1 and also controlling the actuators such as the blood pump 4 and the substitution pump 13. Specifically, in the present embodiment, the control device 20 is capable of initiating a testing process for checking the connection of the substitution line L9 to the collecting port 11. The testing process is performed by forming the pressure-increasing portion including the collecting port 11, increasing the liquid pressure in the pressure-increasing portion, and measuring the pressure with the pressure-measuring device Pc. The pressure-increasing portion, whose liquid pressure is increased in the testing process, includes at least a region from the connection between the collecting port 11 and the substitution line L9 to a portion that is closed by the closing device (in the present embodiment, the substitution pump 13).

The testing process according to the present embodiment is a process performed in a state, illustrated in FIG. 5 for example, where the other end of the branch line L9b included in the substitution line L9 is connected to the distal end (the connector c) of the arterial blood circuit 2a (a state where the substitution line L9 and the blood circuit 2 are filled with a priming solution (the dialysate) (a state after a priming process)). In the testing process, the liquid pressure in the pressure-increasing portion is increased with the liquid-feeding pressure applied from the liquid-feeding device (D). That is, in the testing process according to the present embodiment, the liquid-feeding pressure generated by the liquid-feeding device (D) positioned on the upstream side with respect to the hemodialysis apparatus 1 is utilized for increasing the liquid pressure in the pressure-increasing portion.

More specifically, the testing process according to the present embodiment includes a first checking step (see FIG. 6) of increasing the liquid pressure in the pressure-increasing portion and checking whether or not a pressure higher than or equal to a predetermined value is measured by the pressure-measuring device Pc within a predetermined period of time, and a second checking step (see FIG. 7) of checking whether or not the pressure measured by the pressure-measuring device Pc is retained for a predetermined period of time after the increase of the liquid pressure in the pressure-increasing portion is stopped. Referring to FIG. 10, if there is no liquid leakage from the collecting port 11 and the substitution line L9 is connected normally, the pressure reaches a predetermined value v1 or higher within a predetermined time period t1 in the first checking step as represented by a graph a, and the predetermined value v1 is retained even after the elapse of a predetermined time period t2 in the second checking step. If there is any slight (a very small amount of) liquid leakage from the collecting port 11, the pressure reaches the predetermined value v1 or higher within the predetermined time period t1 in the first checking step but is reduced by a value v2 after the elapse of the predetermined time period t2 as represented by a graph (f3). Hence, by detecting the occurrence of such a pressure reduction (v2), the occurrence of any slight (a very small amount of) liquid leakage from the collecting port 11 can be checked. Of course, a case where the pressure does not reach the predetermined value v1 or higher within the predetermined time period t1 in the first checking step can also be regarded that there is any liquid leakage from the collecting port 11.

Now, a control operation performed in the testing process according to the present embodiment will be described with reference to the flow chart illustrated in FIG. 9.

First, as illustrated in FIG. 6, while the substitution pump 13 and the other pumps are stopped, the electromagnetic valves V1, V3, V6, and V7 are opened, whereas the other electromagnetic valves V2, V4, V5, V8, and V9 are closed, whereby a liquid-feeding pressure is applied to the inside of the pressure-increasing portion from the liquid-feeding device (D) positioned on the upstream side with respect to the tube L1a to which the dialysate introduction line L1 is connected (in the present embodiment, the liquid-feeding device (D) is positioned in the dialysate-supplying apparatus 21) (S1). Note that the clamping device h is closed during the testing process.

Thus, the liquid pressure in the pressure-increasing portion is increased by utilizing the liquid-feeding pressure applied from the liquid-feeding device (D), and whether or not a pressure higher than or equal to a predetermined value is measured by the pressure-measuring device Pc within a predetermined time period is checked (S2) (the first checking step). If it is determined that there is a pressure increase greater than or equal to a predetermined value, the process proceeds to step S3. If it is determined that there is no pressure increase greater than or equal to the predetermined value, the process proceeds to step S10. In step S3, as illustrated in FIG. 7, while the electromagnetic valve V6 is kept open, the other electromagnetic valves V1 to V5 and V7 to V9 are closed. Thus, a closed circuit including the pressure-measuring device Pc is formed. Accordingly, the increase in the liquid pressure (the pressurization) that has been caused by the liquid-feeding device (D) is stopped, and a value (P0) measured by the pressure-measuring device Pc at this point of time is stored (S4).

Subsequently, in step S5, whether or not a predetermined time period has elapsed is checked. If it is determined that the predetermined time period has elapsed, a value (P1) measured by the pressure-measuring device Pc at this point of time is stored (S6). Then, the difference between the value (P0) stored in step S4 and the value (P1) stored in step S6 is calculated, whereby whether or not the pressure is retained for a predetermined time period is checked (S7) (the second checking step). If it is determined that the pressure has been retained, the process proceeds to step (S8), where the pressure in the pressure-increasing portion is released, and the testing process ends. If it is determined that the pressure has not been retained, the process proceeds to step (S9), where warning 1 (a warning notifying that the pressure has not been retained) is generated, and the testing process ends.

In contrast, if it is determined in step (S2) that there is no pressure increase greater than or equal to the predetermined value, the process proceeds to step (S10). In step (S10), as illustrated in FIG. 8, while the substitution pump 13 and the other pumps are kept stopped, the electromagnetic valves V1, V3, V6, and V7 are opened, whereas the other electromagnetic valves V2, V4, V5, V8, and V9 are closed. Then, the value detected by the venous-pressure sensor Pb is monitored, so that whether or not there is any increase in the value detected by the venous-pressure sensor Pb is checked (a third checking step). In this step, the clamping devices 7 and h are closed.

If it is determined in step (S10) that there is an increase in the value detected by the venous-pressure sensor Pb, the process proceeds to step (S11), where warning 2 (a warning notifying that there is a defect in the closing of the substitution pump 13) is generated, and the testing process ends. If it is determined in step (S10) that there is no increase in the value detected by the venous-pressure sensor Pb, the process proceeds to step (S12), where warning 3 (a warning notifying that the substitution line L9 is not connected to the collecting port 11 or is connected but is loose halfway with a leakage) is generated, and the testing process ends.

In the present embodiment, the pressure-measuring device Pc is provided at a position of the dialysate drain line L2 between the connection to the bypass line L5 and the connection to the bypass line L6. Alternatively, as illustrated in FIG. 11, the pressure-measuring device Pc may be provided at a position of the dialysate introduction line L1 between the filtration filter 10 and the branch point f. In that case, in the first checking step, while the substitution pump 13 and the other pumps are stopped as illustrated in FIG. 12, the electromagnetic valves V1, V3, V4, V5 and V7 are opened, whereas the other electromagnetic valves V2, V6, V8, and V9 are closed, whereby the liquid-feeding pressure generated by the liquid-feeding device (D) is applied to the inside of the pressure-increasing portion.

In the present embodiment, the substitution line L9 is provided with the substitution pump 13. Alternatively, as illustrated in FIG. 13, the substitution line L9 may be provided with a clamping device such as an electromagnetic valve V10 that is capable of opening and closing the flow route provided by the substitution line L9. In that case, the electromagnetic valve V10 serves as a closing device that is capable of arbitrarily closing the flow route provided by the substitution line L9 and is configured to form the pressure-increasing portion including the collecting port 11 in the state where the flow route is closed. Furthermore, in the first checking step, while the pumps are stopped as illustrated in FIG. 14, the electromagnetic valves V1, V3, V6, and V7 are opened, whereas the other electromagnetic valves V2, V4, V5, V8, V9, and V10 are closed, whereby the liquid-feeding pressure generated by the liquid-feeding device D is applied to the inside of the pressure-increasing portion.

In the present embodiment, the liquid-feeding pressure generated by the liquid-feeding device (D) is applied through the detour line L4. Alternatively, as illustrated in FIG. 15, a detour line L13 that detours the duplex pump 8 may be provided to the dialysate introduction line L1, and an electromagnetic valve V11 may be provided to the detour line L13. Thus, the liquid-feeding pressure generated by the liquid-feeding device D may be applied through the detour line L13. In that case, in the first checking step as illustrated in FIG. 16, while the substitution pump 13 and the other pumps are stopped, the electromagnetic valves V1, V4, and V11 are opened, whereas the other electromagnetic valves V2, V3, and V5 to V9 are closed. Thus, the liquid-feeding pressure generated by the liquid-feeding device (D) can be applied to the inside of the pressure-increasing portion.

According to the present embodiment, the testing process is performed by increasing the liquid pressure in the pressure-increasing portion by utilizing the liquid-feeding pressure applied from the liquid-feeding device (D) (in the present embodiment, the liquid-feeding device (D) provided in the dialysate-supplying apparatus 21) that is capable of supplying a predetermined liquid at a constant pressure. Therefore, the process of checking the connection of the substitution line L9 to the collecting port 11 can be performed accurately and instantly. Furthermore, the checking process can be performed even during the blood purification treatment. More specifically, the testing process is performed by increasing the liquid pressure in the pressure-increasing portion by utilizing the liquid-feeding pressure generated by activating the non-displacement-type pump that is a turbo-type pump such as a centrifugal pump, an axial-flow pump, or a mixed-flow pump. Therefore, the liquid-feeding pressure for increasing the liquid pressure in the pressure-increasing portion can be obtained with a general-purpose device.

The testing process includes the first checking step of increasing the liquid pressure in the pressure-increasing portion and checking whether or not a pressure higher than or equal to a predetermined value is measured by the pressure-measuring device Pc within a predetermined period of time, and a second checking step of checking whether or not the pressure measured by the pressure-measuring device Pc is retained for a predetermined period of time after the increase of the liquid pressure in the pressure-increasing portion is stopped. Thus, whether or not the pressure-increasing portion is formed normally can be checked in the first checking step, and whether or not the connection of the substitution line L9 to the collecting port 11 is normal can be checked in the second checking step.

In the testing process, if it is determined in the first checking step that no pressure higher than or equal to a predetermined value is measured within a predetermined period of time, the third checking step is performed in which whether or not there is any increase in the value detected by the venous-pressure sensor Pb. Therefore, whether or not the closing by the closing device (the substitution pump 13 or the electromagnetic valve V10) is performed normally can be checked by utilizing the venous-pressure sensor Pb. If it is determined in the first checking step that no pressure higher than or equal to the predetermined value is measured within the predetermined period of time, a predetermined warning may alternatively be generated and the third checking may be omitted.

Now, a blood purification apparatus according to a second embodiment of the present teachings will be described.

The blood purification apparatus is applied to a personal dialysis apparatus and includes, as illustrated in FIG. 17, a blood circuit 2, a dialyzer 3 (a blood purifier), a blood pump 4, an arterial air-trap chamber 5, a venous air-trap chamber 6, a clamping device 7, a duplex pump 8, filtration filters (9 and 10), a collecting port 11, an ultrafiltration pump 12, a substitution pump 13 (a closing device), a dialysate introduction line L1, a dialysate drain line L2, a substitution line L9, a pressure-measuring device Pc, and a control device 20. Elements that are the same as those described in the first embodiment are denoted by corresponding ones of the reference numerals, and detailed description of those elements is omitted.

The personal dialysis apparatus according to the present embodiment includes tanks T1 and T2 each containing undiluted dialysate and connected to the dialysate introduction line L1 with introduction lines L14 and L15, respectively. The introduction lines L14 and L15 are provided with pumps M1 and M2, respectively, each being capable of introducing the undiluted dialysate contained in a corresponding one of the tanks T1 and T2 into the dialysate introduction line L1. The dialysate introduction line L1 is further provided with a mixing chamber C1 for mixing the undiluted dialysate in the tank T1, and a mixing chamber C2 for mixing the undiluted dialysate in the tank T2.

The dialysate introduction line L1 according to the present embodiment is connected to the water treatment apparatus 23. When the liquid-feeding device D provided in the water treatment apparatus 23 is activated, the clean water generated by the water treatment apparatus 23 is supplied to the dialysate introduction line L1, and the undiluted dialysate in the tanks T1 and T2 and the clean water are mixed together, whereby a dialysate having a predetermined concentration is prepared. The dialysate having a predetermined concentration thus prepared while flowing through the dialysate introduction line L1 is introduced into the dialyzer 3 (the blood purifier) and is used for the blood purification treatment.

In the present embodiment, as with the first embodiment, a testing process is performed by increasing the liquid pressure in the pressure-increasing portion by utilizing the liquid-feeding pressure applied from the liquid-feeding device (D) (the liquid-feeding device (D) provided in the water treatment apparatus 23). For example, as illustrated in FIG. 18, while the substitution pump 13 and the other pumps are stopped, the electromagnetic valves V1, V3, V6, and V7 are opened, whereas the other electromagnetic valves V2, V4, V5, V8, and V9 are closed, whereby the liquid-feeding pressure generated by the liquid-feeding device (D) included in the water treatment apparatus 23 positioned on the upstream side with respect to the dialysate introduction line L1 is applied to the inside of the pressure-increasing portion. Thus, the first checking step can be performed in which the liquid pressure in the pressure-increasing portion is increased and whether or not a pressure higher than or equal to a predetermined value is measured by the pressure-measuring device Pc within a predetermined period of time is checked.

If it is determined in the first checking step that there is a pressure increase greater than or equal to a predetermined value, the second checking step can be performed in which, as illustrated in FIG. 19, the electromagnetic valve V6 that is open is kept open while the other electromagnetic valves V1 to V5 and V7 to V9 are closed, and whether or not the value measured by the pressure-measuring device Pc is retained for a predetermined period of time is checked. If it is determined in the first checking step that no pressure higher than or equal to the predetermined value is measured within the predetermined period of time, a third checking step may be performed in which the other end of the substitution line L9 is connected to an upper part of the venous air-trap chamber 6, and whether or not there is any increase in the value detected by the venous-pressure sensor Pb is checked.

According to the present embodiment, as with the first embodiment, the testing process is performed by increasing the liquid pressure in the pressure-increasing portion by utilizing the liquid-feeding pressure applied from the liquid-feeding device (D) (in the present embodiment, the liquid-feeding device (D) provided in the water treatment apparatus 23) that is capable of supplying a predetermined liquid at a constant pressure. Therefore, the process of checking the connection of the substitution line L9 to the collecting port 11 can be performed accurately and instantly. Furthermore, the checking can be performed even during the blood purification treatment. More specifically, the testing process is performed by increasing the liquid pressure in the pressure-increasing portion by utilizing the liquid-feeding pressure generated by activating the non-displacement-type pump that is a turbo-type pump such as a centrifugal pump, an axial-flow pump, or a mixed-flow pump. Therefore, the liquid-feeding pressure for increasing the liquid pressure in the pressure-increasing portion can be obtained with a general-purpose device.

In the present embodiment, the valve devices (the electromagnetic valves V1 to V9) that are capable of opening and closing the liquid flow route are each provided with electrical-continuity sensors e (concentration cells), whereby the open/closed state of each of the valve devices can be detected. The dialysate is a conductive liquid. Therefore, if a voltage is applied to the electrical-continuity sensors (e) when a corresponding one of the valve devices (the electromagnetic valves V1 to V9), which are insulators, is open, the electrical-continuity sensors e become electrically continuous with each other. In contrast, if a voltage is applied to the electrical-continuity sensors e when the corresponding valve device is closed, the electrical-continuity sensors (e) do not become electrically continuous with each other. That is, the open/closed state can be detected on the basis of whether or not an electrical-continuity signal is generated.

Utilizing the electrical-continuity sensors (e) provided for the valve devices (the electromagnetic valves V1 to V9), whether or not a washing process is necessary after the testing process may be checked. Specifically, if the dialysate, which is conductive, is present in the flow route, the electrical-continuity sensors e become electrically continuous with each other with the application of a voltage. If the clean water, which is non-conductive, is present in the flow route, the electrical-continuity sensors e do not become electrically continuous with each other even with the application of a voltage. Therefore, the switching of the electrical-continuity signal from the on-state to the off-state can be detected as the point of time when the dialysate is substituted by the clean water. Hence, if the testing process is performed with any leakage occurring at the collecting port 11, the dialysate in the dialysate introduction line L1 is substituted by the clean water supplied from the liquid-feeding device (D). Accordingly, if the substitution is detected by the electrical-continuity sensors (e) provided for the valve devices (the electromagnetic valves V1 to V9), the washing process in which the dialysate introduction line L1 is washed with the clean water is performed.

According to the present embodiment, the dialysate introduction line L1 is supplied with the clean water from the liquid-feeding device D and also with the undiluted dialysate. The clean water and the undiluted dialysate are mixed together into a dialysate that is to be introduced into the dialyzer 3. In addition, the dialysate introduction line L1 is provided with the electrical-continuity sensors (e) that are capable of identifying which of the clean water and the dialysate is present by checking whether or not there is electrical continuity at the application of a voltage. If what is identified is the clean water, the washing process in which the dialysate introduction line L1 is washed with the clean water is performed. Therefore, in the so-called personal apparatus, the entry of clean water into the dialysate introduction line L1 can be recognized through the testing process, and the washing process can be performed automatically.

The electrical-continuity sensors e according to the present embodiment are provided for the valve devices (the electromagnetic valves V1 to V9) that are capable of opening and closing the liquid flow route. The electrical-continuity sensors (e) are capable of detecting the open/closed state of the valve devices by checking whether or not there is electrical continuity therebetween at the application of a voltage. Therefore, the electrical-continuity sensors e can have both the function of detecting the open/closed state of the valve devices and the function of recognizing the entry of clean water into the dialysate introduction line L1. Note that the electrical-continuity sensors (e) may be provided independently of the valve devices.

While some embodiments have been described above, the present teachings are not limited thereto. For example, as illustrated in FIG. 20, the duplex pump 8 may be replaced with a balancing chamber 24 including a first chamber 24a and a second chamber 24b. In that case, if the electromagnetic valves V1, Va, Vb, and V4 are opened while the other electromagnetic valves V2, V3, V5 to V9, and Vc to Vh are closed with the substitution pump 13 and the other pumps being stopped, the liquid-feeding pressure generated by the liquid-feeding device (D) positioned on the upstream side with respect to the dialysate introduction line L1 can be applied to the inside of the pressure-increasing portion.

Alternatively, as illustrated in FIG. 21, a storage tank 25 storing the dialysate may be provided at a position above the hemodialysis apparatus 1 so that a liquid-feeding pressure generated by the level difference can be utilized for increasing the liquid pressure in the pressure-increasing portion when the testing process is performed. In that case, if the electromagnetic valves V1, V3, V4, V5, and V7 are opened while the other electromagnetic valves V2, V6, V8, and V9 are closed with the substitution pump 13 and the other pumps being stopped, the liquid-feeding pressure generated in the liquid-feeding device (the storage tank 25) positioned on the upstream side with respect to the dialysate introduction line L1 can be applied to the inside of the pressure-increasing portion. Thus, the liquid-feeding pressure for increasing the liquid pressure in the pressure-increasing portion can be obtained with a general-purpose device, without using any device such as a pump.

The liquid-feeding device (D) is not limited to be provided in the dialysate-supplying apparatus 21 or the water treatment apparatus 23, as long as it is positioned on the upstream side with respect to the dialysate introduction line L1. For example, the liquid-feeding device (D) may be provided at any position between the dialysate-supplying apparatus 21 or the water treatment apparatus 23 and the connection thereof to the dialysate introduction line L1. In addition, the testing process may be any other type of process (such as a testing process including only the first checking step, or a testing process including only the second checking step), as long as the connection of the substitution line L9 to the collecting port 11 is checked by increasing the liquid pressure in the pressure-increasing portion by utilizing the liquid-feeding pressure applied from the liquid-feeding device D and measuring the pressure with the pressure-measuring device Pc.

The present teachings may be applied to any blood purification apparatus having other additional functions or the like, as long as the apparatus performs a testing process in which the liquid pressure in a pressure-increasing portion is increased by utilizing the liquid-feeding pressure applied from a liquid-feeding device.

REFERENCE SIGN LIST 1 hemodialysis apparatus (blood purification apparatus)
2 blood circuit
2a arterial blood circuit
2b venous blood circuit
3 dialyzer (blood purifier)
4 blood pump
5 arterial air-trap chamber
6 venous air-trap chamber
7 clamping device
8 duplex pump
9, 10 filtration filter
11 collecting port
12 ultrafiltration pump
13 substitution pump
L1 dialysate introduction line
L2 dialysate drain line
L9 substitution line
Pc pressure-measuring device

The invention claimed is:
1. A blood purification apparatus comprising:
a blood circuit including an arterial blood circuit and a venous blood circuit and through which blood of a patient is allowed to extracorporeally circulate;
a blood purifier connected to the blood circuit that is capable of purifying the blood extracorporeally while circulating through the blood circuit;
a dialysate introduction line supplied with a predetermined liquid from a liquid-feeding device and through which a dialysate is introduced into the blood purifier, the liquid-feeding device being capable of feeding the liquid at a constant pressure;
a dialysate drain line through which waste water is discharged from the blood purifier;
a substitution line one end of which is connected to a collecting port provided at a predetermined position of the dialysate introduction line and an other end of which is connected to the arterial blood circuit or the venous blood circuit;
a displacement-type pump provided on the dialysate introduction line or the substitution line:

a closing device provided to the substitution line and that is capable of arbitrarily closing a flow route provided by the substitution line, the closing device being configured to form, in a state where the flow route is closed, a pressure-increasing portion that includes the collecting port; and a pressure-measuring device capable of measuring a pressure in the pressure-increasing portion, the blood purification apparatus performing a testing process in which connection of the substitution line to the collecting port is checked by increasing a liquid pressure in the pressure-increasing portion and measuring the pressure with the pressure-measuring device, wherein the testing process is performed by increasing the liquid pressure in the pressure-increasing portion by utilizing a liquid-feeding pressure applied from the liquid-feeding device, and the liquid-feeding device generates the liquid-feeding pressure by activation of a non-displacement-type or a level difference of the dialysate in the liquid-feeding device relative to the dialysate in the pressure-increasing portion and not by the displacement-type pump.

2. The blood purification apparatus according to claim 1, wherein the non-displacement-type pump is a turbo-type pump.

3. The blood purification apparatus according to claim 1, wherein the testing process includes:

a first checking step of increasing the liquid pressure in the pressure-increasing portion and checking whether or not a pressure higher than or equal to a predetermined value is measured by the pressure-measuring device within a predetermined period of time; and a second checking step of checking whether or not the pressure measured by the pressure-measuring device is retained for a predetermined period of time after the increase of the liquid pressure in the pressure-increasing portion is stopped.

4. The blood purification apparatus according to claim 3, wherein the venous blood circuit is provided with a venous-pressure sensor that is capable of detecting, during blood purification treatment, a venous pressure of the blood that is under extracorporeal circulation, and wherein the testing process further includes a third checking step in which if it is determined in the first checking step that the pressure higher than or equal to the predetermined value is not measured within the predetermined period of time, whether or not there is an increase in the pressure detected by the venous-pressure sensor is checked.

5. The blood purification apparatus according to claim 1, wherein the dialysate introduction line is supplied with clean water from the liquid-feeding device and with undiluted dialysate, the clean water and the undiluted dialysate being mixed together into the dialysate that is to be introduced into the blood purifier, wherein the dialysate introduction line is provided with an electrical-continuity sensor that is capable of identifying which of the clean water and the dialysate is present by checking whether or not there is electrical continuity at an application of a voltage, and wherein if what is identified is the clean water, a washing process in which the dialysate introduction line is washed with the clean water is performed.

6. The blood purification apparatus according to claim 5, wherein the electrical-continuity sensor is provided to a valve device that is capable of opening and closing the flow route of the liquid, and the electrical-continuity sensor is capable of detecting an open or closed state of the valve device by checking whether or not there is electrical continuity at the application of the voltage.

7. The blood purification apparatus according to claim 2, wherein the turbo-type pump is a centrifugal pump, an axial-flow pump, or a mixed-flow pump.

8. The blood purification apparatus according to claim 1, wherein the substitution line includes a branch line extending from a branch point, the branch line includes a clamping device that opens and closes the branch line.

9. The blood purification apparatus according to claim 1, wherein a first end of a branch line is connected to a venous air-trap chamber or an arterial air-trap chamber.

10. The blood purification apparatus according to claim 1, wherein a second end of a branch line is connected to a connector at a distal end of the arterial blood circuit.

11. The blood purification apparatus according to claim 9, wherein a second end of the branch line is connected to a connector at a distal end of the arterial blood circuit.

12. The blood purification apparatus according to claim 1, wherein the substitution line includes a substitution pump located upstream of a branch point.

13. The blood purification apparatus according to claim 12, wherein the substitution pump is a closing device, when the substitution pump is stopped, so that the substitution pump forms part of the pressure-increasing portion at the collecting port when the flow route is closed.

14. The blood purification apparatus according to claim 1, wherein a duplex pump extends between and connects the dialysate introduction line and the dialysate drain line.

15. The blood purification apparatus according to claim 14, wherein the duplex pump supplies the dialysate having a predetermined concentration from the liquid-feeding device to a dialyzer while discharging the waste water from the dialyzer.

16. The blood purification apparatus according to claim 14, wherein a bypass line forms a flow route connecting the dialysate introduction line and the dialysate drain line together and the bypass line is located upstream of the duplex pump.

17. The blood purification apparatus according to claim 16, wherein a first bypass line forms a flow route connecting the dialysate introduction line and the dialysate drain line together and the first bypass line is located downstream of the bypass line and the duplex pump.

18. The blood purification apparatus according to claim 17, wherein a second bypass line forms a flow route connecting the dialysate introduction line and the dialysate drain line together and the second bypass line is located downstream of the bypass line, the first bypass line, and the duplex pump.

19. The blood purification apparatus of claim 1, wherein the liquid feeding device includes a storage tank that stores the dialysate and the storage tank is located above the pressure-increasing portion so that pressure is generated.

* * * * *